United States Patent
Cole et al.

(10) Patent No.: US 9,855,249 B2
(45) Date of Patent: Jan. 2, 2018

(54) ISOXAZOLE COMPOUNDS AND METHODS FOR THE TREATMENT OF CYSTIC FIBROSIS

(71) Applicant: FLATLEY DISCOVERY LAB, LLC, Charlestown, MA (US)

(72) Inventors: Bridget M. Cole, Quincy, MA (US); Andrew Kolodziej, Winchester, MA (US)

(73) Assignee: FLATLEY DISCOVERY LAB, LLC, Charlestown, MA (US)

(*) Notice: Subject to any disclaimer, the term of this patent is extended or adjusted under 35 U.S.C. 154(b) by 0 days.

(21) Appl. No.: 14/873,933

(22) Filed: Oct. 2, 2015

(65) Prior Publication Data

US 2016/0128984 A1 May 12, 2016

Related U.S. Application Data

(60) Provisional application No. 62/058,938, filed on Oct. 2, 2014.

(51) Int. Cl.

| | | |
|---|---|---|
| *A61K 31/422* | (2006.01) | |
| *C07D 413/12* | (2006.01) | |
| *A61K 31/42* | (2006.01) | |
| *A61K 31/4439* | (2006.01) | |
| *A61K 31/454* | (2006.01) | |
| *A61K 31/47* | (2006.01) | |
| *A61K 31/496* | (2006.01) | |
| *A61K 31/5377* | (2006.01) | |
| *A61K 31/55* | (2006.01) | |
| *A61K 31/551* | (2006.01) | |
| *C07D 261/18* | (2006.01) | |

(52) U.S. Cl.
CPC ............ *A61K 31/422* (2013.01); *A61K 31/42* (2013.01); *A61K 31/4439* (2013.01); *A61K 31/454* (2013.01); *A61K 31/47* (2013.01); *A61K 31/496* (2013.01); *A61K 31/5377* (2013.01); *A61K 31/55* (2013.01); *A61K 31/551* (2013.01); *C07D 261/18* (2013.01); *C07D 413/12* (2013.01)

(58) Field of Classification Search
CPC ........................... A61K 31/422; C07D 413/12
See application file for complete search history.

(56) References Cited

U.S. PATENT DOCUMENTS

| | | |
|---|---|---|
| 6,518,264 B2 | 2/2003 | Achard et al. |
| 7,094,777 B2 | 8/2006 | Chambers et al. |
| 2005/0085424 A1 | 4/2005 | Sato et al. |
| 2009/0203690 A1 | 8/2009 | Akritopoulou-Zanze et al. |
| 2009/0239810 A1 | 9/2009 | Sundaresan et al. |
| 2011/0245221 A1 | 10/2011 | Giannini et al. |
| 2011/0306587 A1 | 12/2011 | Allen et al. |
| 2012/0046266 A1 | 2/2012 | Brasca et al. |

FOREIGN PATENT DOCUMENTS

| | | |
|---|---|---|
| EP | 0 930 313 A1 | 7/1999 |
| JP | H0827130 A | 1/1996 |
| JP | 2005060379 A | 3/2005 |
| WO | 2008/070739 A1 | 6/2008 |
| WO | 2015/138909 A1 | 9/2015 |
| WO | 2016/105468 A1 | 6/2016 |
| WO | 2016/105477 A1 | 6/2016 |
| WO | 2016/105484 A1 | 6/2016 |
| WO | 2016/105485 A2 | 6/2016 |
| WO | 2016/115090 A1 | 7/2016 |

OTHER PUBLICATIONS

Yoshikawa, et al., J. Med. Chem., 56: 4236-4251 (2013).
RN 1432307-47-5, STN Entry Date May 23, 2013; RN 1396677-89-6, STN Entry Date Sep. 26, 2012; RN 1363716-04-4, STN Entry Date Mar. 30, 2012; RN 1327884-01-4, STN Entry Dare Sep. 4, 2011; RN 1325067-14-8, STN Entry Date Aug. 29, 2011; RN 1252522-65-8, SRN Entry Date Nov. 10, 2010; RN 1252313-84-0, STN Entry Date Nov. 10, 2010; RN 1235072-36-2, STN Entry Date Aug. 5, 2010; RN 1199527-32-6, SRN Entry Date Dec. 30, 2009; RN 1061523-55-4, STN Entry Date Oct. 15, 2008; RN 176593-45-6, STN Entry Date May 23, 1996.

*Primary Examiner* — Golam M M Shameem
(74) *Attorney, Agent, or Firm* — Elmore Patent Law Group, P.C.; Edgar Harlan; Carolyn Elmore

(57) ABSTRACT

The invention relates to a compound of Formula I and methods of treating cystic fibrosis comprising the step of administering a therapeutically effective amount of a compound of Formula I or II to a patient in need thereof:

Formula I

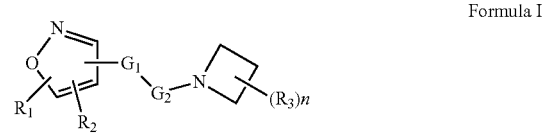

Formula II

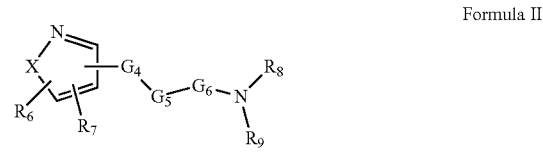

16 Claims, No Drawings

ISOXAZOLE COMPOUNDS AND METHODS FOR THE TREATMENT OF CYSTIC FIBROSIS

RELATED APPLICATION

This application claims the benefit of U.S. Provisional Application No. 62/058,938, filed on Oct. 2, 2014. The entire teachings of the above application are incorporated herein by reference.

BACKGROUND

Cystic fibrosis (CF) is a lethal, recessive, genetic disease affecting approximately 1 in 2500 live births among Caucasians. (Cohen-Cymberknoh, M. et al., *Am. J. Respir. Crit. Care Med.* 1463-1471, 2011; Boat et al., The Metabolic Basis of Inherited Disease, 6th ed., pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. (Hantash F: U.S. Patent Application No. 20060057593). The CF gene codes for a cAMP/PKA-dependent, ATP-requiring, membrane chloride ion channel, generally found in the apical membranes of many secreting epithelia and is known as CFTR (cystic fibrosis transmembrane conductance regulator). There are currently over 1900 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cuthbert A W, *British Journal of Pharmacology*, 163(1), 173-183, 2011).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et al., *Am. J. Respir. Crit. Care Med.* 1463-1471, 2011).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et al., *Expert Opin Pharmacother.* 10(7), 1191-202, 2009).

SUMMARY

The invention relates to the use of substituted oxazole and substituted thiazole compounds in the treatment of cystic fibrosis transmembrane conductance regulator (CFTR) mediated diseases. The invention relates to a compound of Formula I or II and methods of treating CFTR mediated diseases, in particular cystic fibrosis, comprising the step of administering a therapeutically effective amount of a compound of Formula I or II to a patient in need thereof:

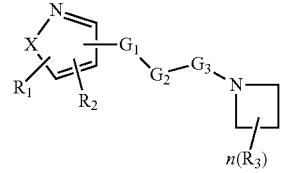

Formula I

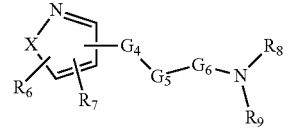

Formula II

DETAILED DESCRIPTION OF THE INVENTION

In one embodiment, the invention relates to a compound of Formula I and methods of treating cystic fibrosis comprising the step of administering a therapeutically effective amount of a compound of Formula I to a patient in need thereof:

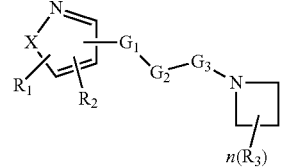

Formula I or a pharmaceutically acceptable salt, ester of prodrug thereof;

wherein, X is S or O;

$G_1$ is selected from absent, —C(O)N($R_{10}$)—, —C(S)N($R_{10}$)—, —N($R_{10}$)—, —C(O)O—, —C(O)—, —C(S)—, —N($R_{11}$)C(O)N($R_{10}$)—, —S—, —O—, —SO—, —S(O)$_2$—, —S(O)$_2$N($R_{10}$)—, —C(S)O— and —C(S)N($R_{10}$);

each $R_{10}$ and $R_{11}$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

each G₂ is absent or is selected from a bivalent aliphatic, substituted aliphatic, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl;

G₃ is absent or is selected from absent, —N(R₁₀)C(O)—, —N(R₁₀)C(S)—, —OC(O)—, —C(O)—, —C(S)—, —N(R₁₁)C(O)—, —SO—, —S(O)₂—, —N(R₁₀)S(O)₂—, —OC(S)— and —N(R₁₀)C(S)—;

R₁ is selected from aryl, substituted aryl, heterocyclyl, substituted heterocyclyl, heteroaryl, and substituted heteroaryl;

each R₂ and R₃ is independently selected from hydrogen, halogen, —OR₁₀, —SR₁₀, —NR₁₀R₁₁, —CF₃, —CN, —NO₂, —N₃, —C(O)OR₁₀, —C(O)R₁₀, —C(O)NR₁₀R₁₁, —S(O)R₁₀, —S(O)NR₁₀, —S(O)₂R₁₀, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; and, n is 0, 1, 2, 3, 4, 5 or 6.

In a preferred embodiment, G₁ is selected from —C(O)N(R₁₀)—, —C(S)N(R₁₀)—, —N(R₁₀)—, —C(O)O—, —C(O)—, —C(S)—, —N(R₁₁)C(O)N(R₁₀)—, —S—, —O—.

In a preferred embodiment, G₂ is selected from:

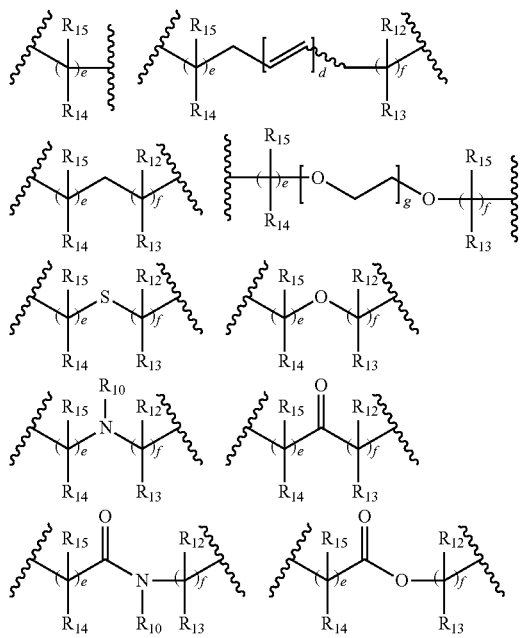

wherein
g is an integer between about 1 and about 1000, preferably between 1 and 100, more preferably between 1 and 10;
e and f is independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30;
d is 1, 2, 3, 4, 5, 6 or 7;
each R₁₂, R₁₃, R₁₄, R₁₅, and R₁₆ is independently selected from absent, hydrogen, halogen, —OR₂₀, —SR₂₀, —NR₂₀R₂₁, —C(O)R₂₀, —C(O)OR₂₀, —C(O)NR₂₀R₂₁, —N(R₂₀)C(O)R₂₁, —CF₃, —CN, —NO₂, —N₃, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; alternatively two R₁₀, R₁₁, R₁₂, R₁₃, R₁₄, R₁₅, and R₁₆ together with the atoms to which they are attached form an optionally substituted 3, 4, 5, 6 or 7 membered ring; and, each R₂₀ and R₂₁ is selected from hydrogen, halogen, aliphatic, substituted aliphatic, aryl or substituted aryl.

In a preferred embodiment, the invention relates to a compound of Formula IA or a pharmaceutical acceptable salt thereof, and methods of treating cystic fibrosis comprising the step of administering a therapeutically effective amount of a compound of Formula IA to a patient in need thereof:

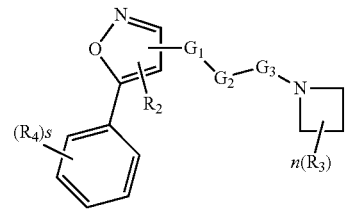

Formula IA wherein, s is 1, 2, 3 or 4;
R₄ is hydrogen, halogen, —OR₂₀, —SR₂₀, —NR₂₀R₂₁, —C(O)R₂₀, —C(O)OR₂₀, —C(O)NR₂₀R₂₁, —N(R₂₀)C(O)R₂₁, —CF₃, —CN, —NO₂, —N₃, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; Alternatively two R₄ together with the atoms to which they are attached form an optionally substituted 3, 4, 5, 6 or 7 membered ring; and, each R₂₀ and R₂₁ is selected from hydrogen, halogen, aliphatic, substituted aliphatic, aryl or substituted aryl.

In a preferred embodiment, the invention relates to a compound of Formula IB, IC, ID or a pharmaceutical acceptable salt thereof, and methods of treating cystic fibrosis comprising the step of administering a therapeutically effective amount of a compound of Formula IB to a patient in need thereof:

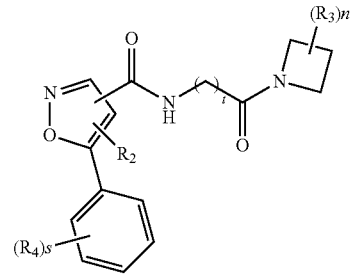

Formula IB

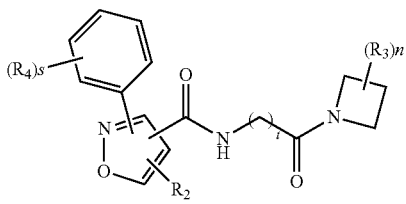

Formula IC

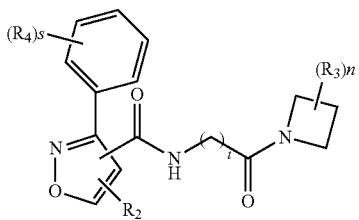

Formula ID wherein t is 1, 2, 3, 4, 5, 6, 7, 8, 9, 10, 11, 12, 13, 14, 15, 16 or 17.

In one embodiment, the invention relates to a compound of Formula II or a pharmaceutical acceptable salt thereof, and methods of treating cystic fibrosis comprising the step of administering a therapeutically effective amount of a compound of Formula II to a patient in need thereof:

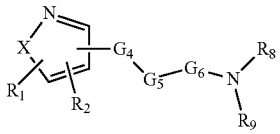

Formula II wherein, X is S or O;

$G_4$ is absent or is selected from absent, —C(O)N($R_{10}$)—, —C(S)N($R_{10}$)—, —N($R_{10}$)—, —C(O)O—, —C(O)—, —C(S)—, —N($R_{11}$)C(O)N($R_{10}$)—, —S—, —O—, —SO—, —S(O)$_2$—, —S(O)$_2$N($R_{10}$)—, —C(S)O— and —C(S)N($R_{10}$);

each $R_{10}$ and $R_{11}$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

each $G_5$ is absent or is selected from a bivalent aliphatic, substituted aliphatic, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl;

$G_6$ is absent or is selected from —N($R_{10}$)C(O)—, —N($R_{10}$)C(S)—, —OC(O)—, —C(O)—, —C(S)—, —N($R_{11}$)C(O)—, —SO—, —S(O)$_2$—, —N($R_{10}$)S(O)$_2$—, —OC(S)— and —N($R_{10}$)C(S)—;

each $R_6$ and $R_7$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; alternatively $R_6$ and $R_7$ together with the atoms to which they are attached form an optionally substituted 3, 4, 5, 6 or 7 membered ring and, each $R_8$ and $R_9$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively $R_8$ and $R_9$ groups together with the nitrogen atom to which they are attached form an optionally substituted 3, 4, 5, 6 or 7 membered ring.

In a preferred embodiment, $G_4$ is selected from —C(O)N($R_{10}$)—, —C(S)N($R_{10}$)—, —N($R_{10}$)—, —C(O)O—, —C(O)—, —C(S)—, —N($R_{11}$)C(O)N($R_{10}$)—, —S—, —O—.

In a preferred embodiment, $G_5$ is selected from:

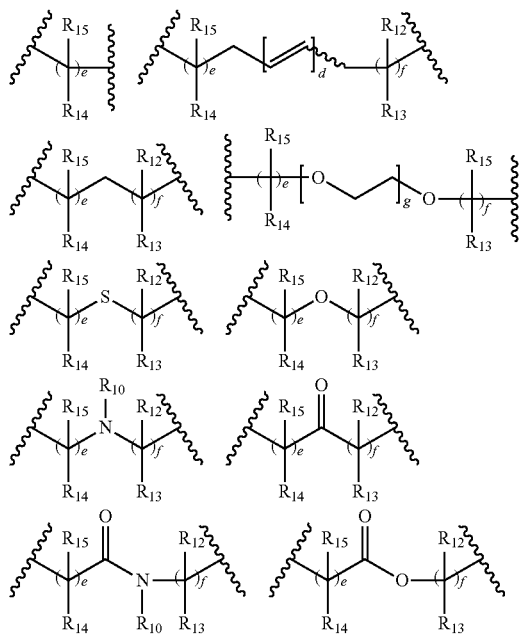

wherein g is an integer between about 1 and about 1000, preferably between 1 and 100, preferably between 1 and 10;

e and f is independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30;

d is 1, 2, 3, 4, 5, 6 or 7;

each $R_{12}$, $R_{13}$, $R_{14}$, and $R_{15}$, is independently selected from absent, hydrogen, halogen, —O$R_{20}$, —S$R_{20}$, —N$R_{20}R_{21}$, —C(O)$R_{20}$, —C(O)O$R_{20}$, —C(O)N$R_{20}R_{21}$, —N($R_{20}$)C(O)$R_{21}$, —CF$_3$, —CN, —NO$_2$, —N$_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; alternatively two $R_{10}$, $R_{11}$, $R_{12}$, $R_{13}$, $R_{14}$, and $R_{15}$ together with the atoms to which they are attached form an optionally substituted 3, 4, 5, 6 or 7 membered ring; and, each $R_{20}$ and $R_{21}$ is selected from hydrogen, halogen, aliphatic, substituted aliphatic, aryl or substituted aryl.

In a preferred embodiment, the invention relates to a compound of Formula I or II or a pharmaceutically acceptable salt thereof, wherein $R_1$ is selected from Table 1:

TABLE 1
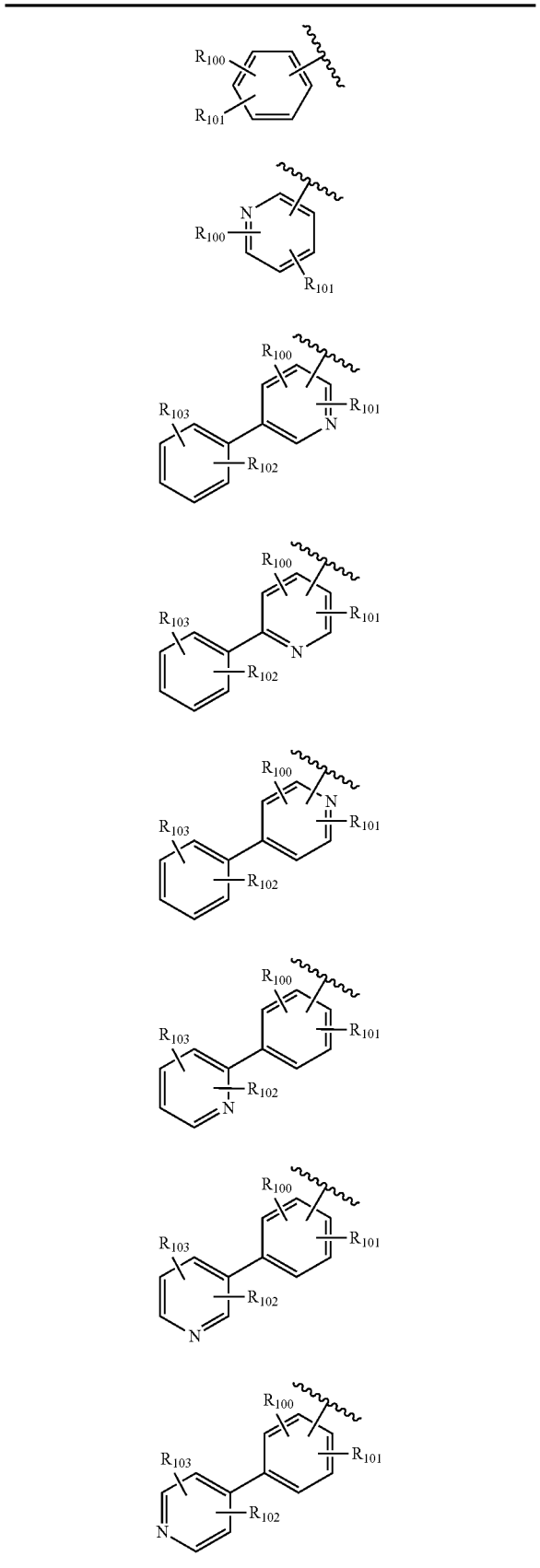
TABLE 1-continued
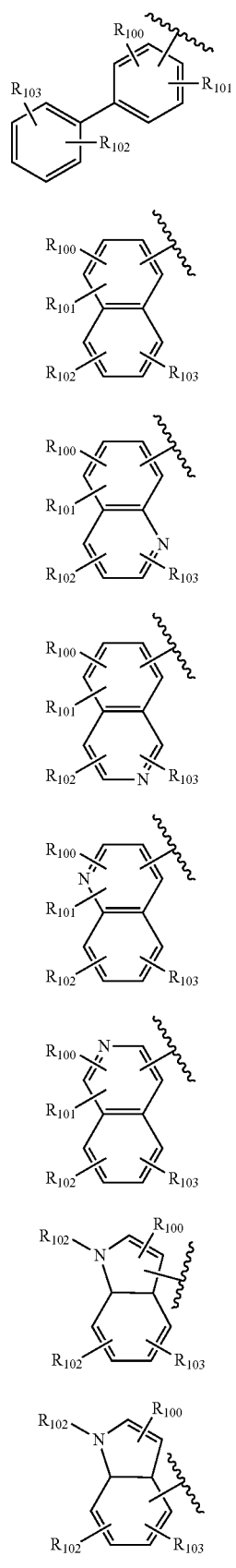

wherein each $R_{100}$, $R_{101}$, $R_{102}$ and $R_{103}$ is independently absent, hydrogen, halogen, —$OR_{10}$, —$SR_{10}$, —$NR_{10}R_{11}$, —$C(O)R_{10}$, —$C(O)OR_{10}$, —$C(O)NR_{10}R_{11}$, —$N(R_{10})C(O)R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl and substituted aryl.

In a preferred embodiment, the invention relates to a compound of Formula I or II or a pharmaceutically acceptable salt thereof, wherein $R_1$ is selected a group below:

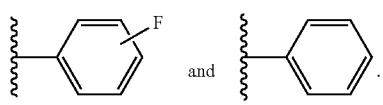

In a preferred embodiment, the invention relates a compound of Formula II wherein $R_8$ and $R_9$ groups together with the nitrogen atom to which they are attached form a cyclic group selected from:

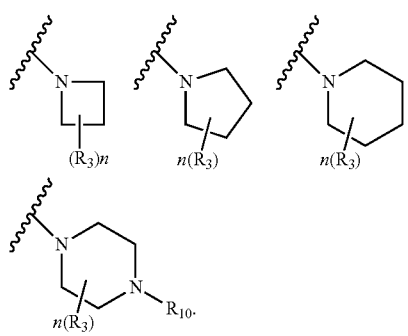

In a more preferred embodiment, a compound of Formula I is selected from Table A or a pharmaceutically acceptable salt thereof:

TABLE A

TABLE A-continued

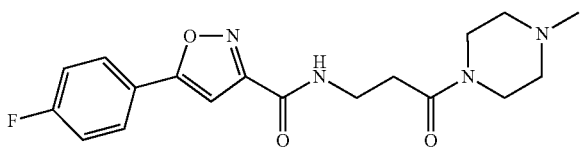 [SMILES: CN1CCN(C(=O)CCNC(=O)c2cc(-c3ccc(F)cc3)on2)CC1]

In a more preferred embodiment, a compound of Formula II is selected from Table B or a pharmaceutically acceptable salt thereof:

TABLE B

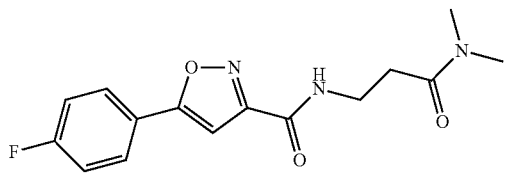 [SMILES: CN(C)C(=O)CCNC(=O)c1cc(-c2ccc(F)cc2)on1]

TABLE B-continued
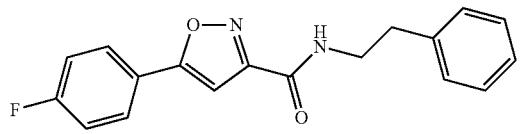 [SMILES: O=C(NCCc1ccccc1)c1cc(-c2ccc(F)cc2)on1]
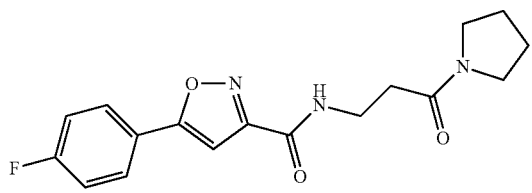 [SMILES: O=C(NCCC(=O)N1CCCC1)c1cc(-c2ccc(F)cc2)on1]
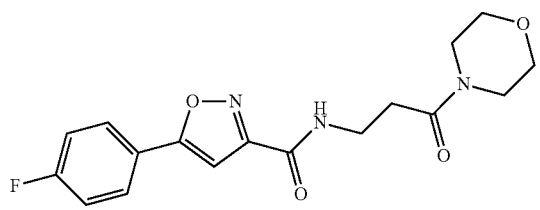 [SMILES: O=C(NCCC(=O)N1CCOCC1)c1cc(-c2ccc(F)cc2)on1]
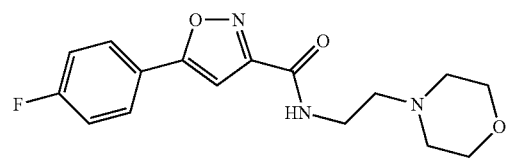 [SMILES: O=C(NCCN1CCOCC1)c1cc(-c2ccc(F)cc2)on1]
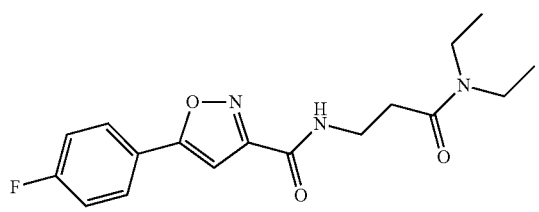 [SMILES: CCN(CC)C(=O)CCNC(=O)c1cc(-c2ccc(F)cc2)on1]
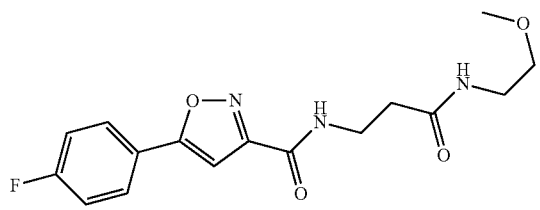 [SMILES: COCCNC(=O)CCNC(=O)c1cc(-c2ccc(F)cc2)on1]
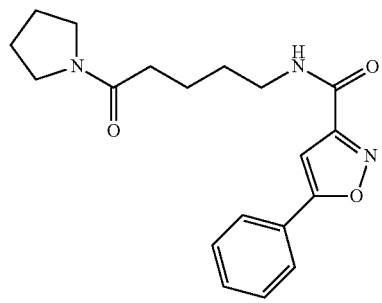 [SMILES: O=C(NCCCCC(=O)N1CCCC1)c1cc(-c2ccccc2)on1]

TABLE B-continued
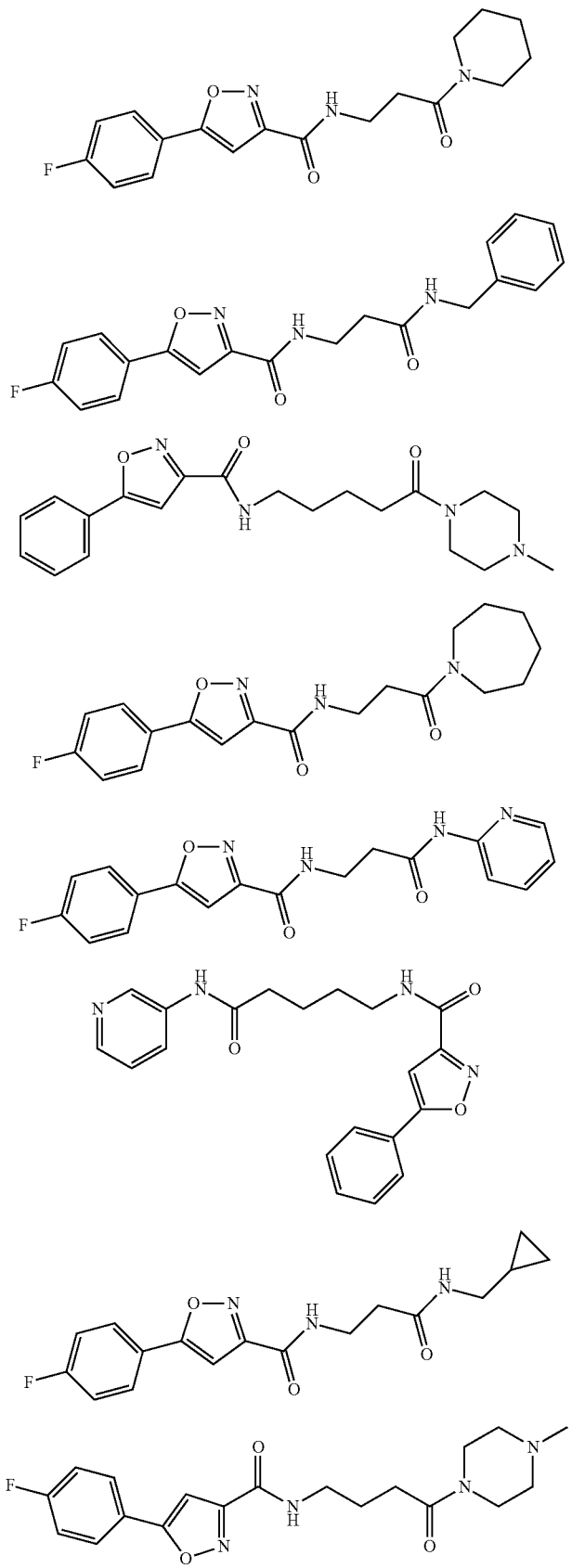

TABLE B-continued
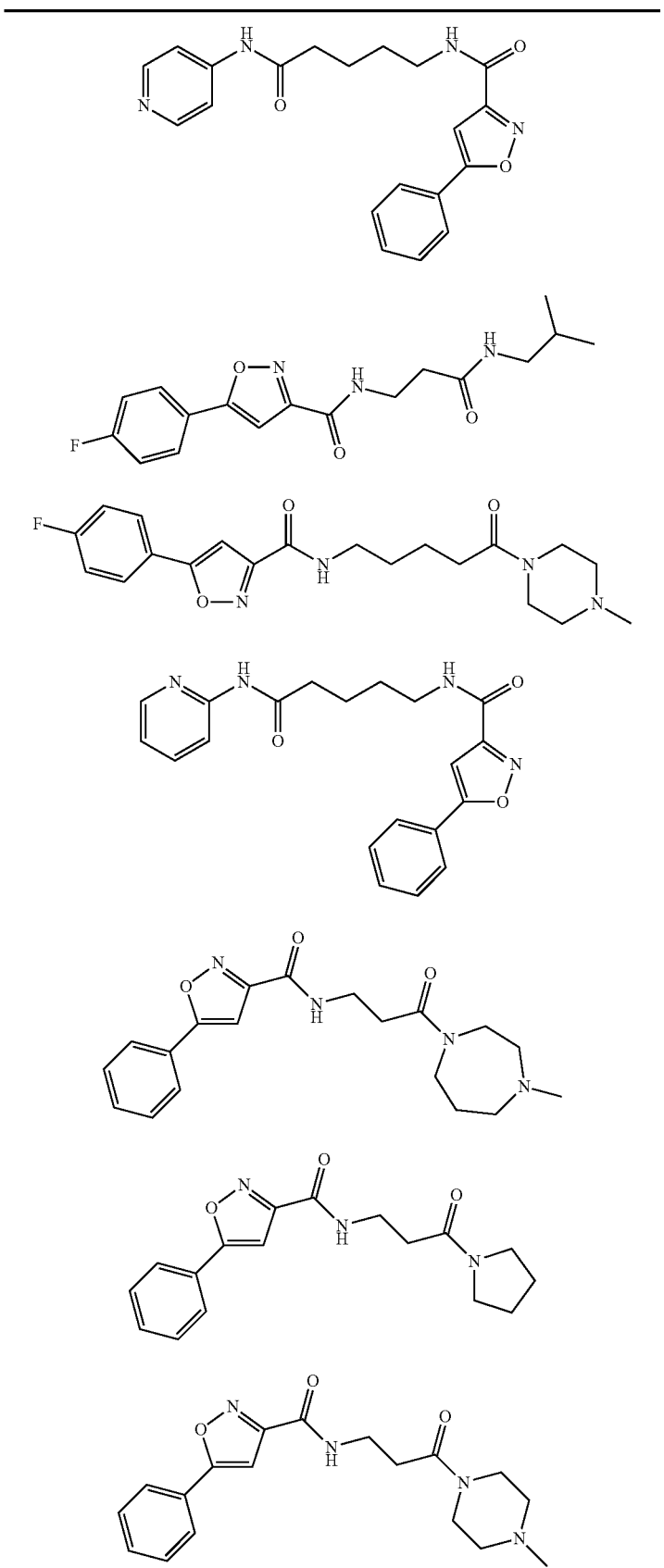

TABLE B-continued
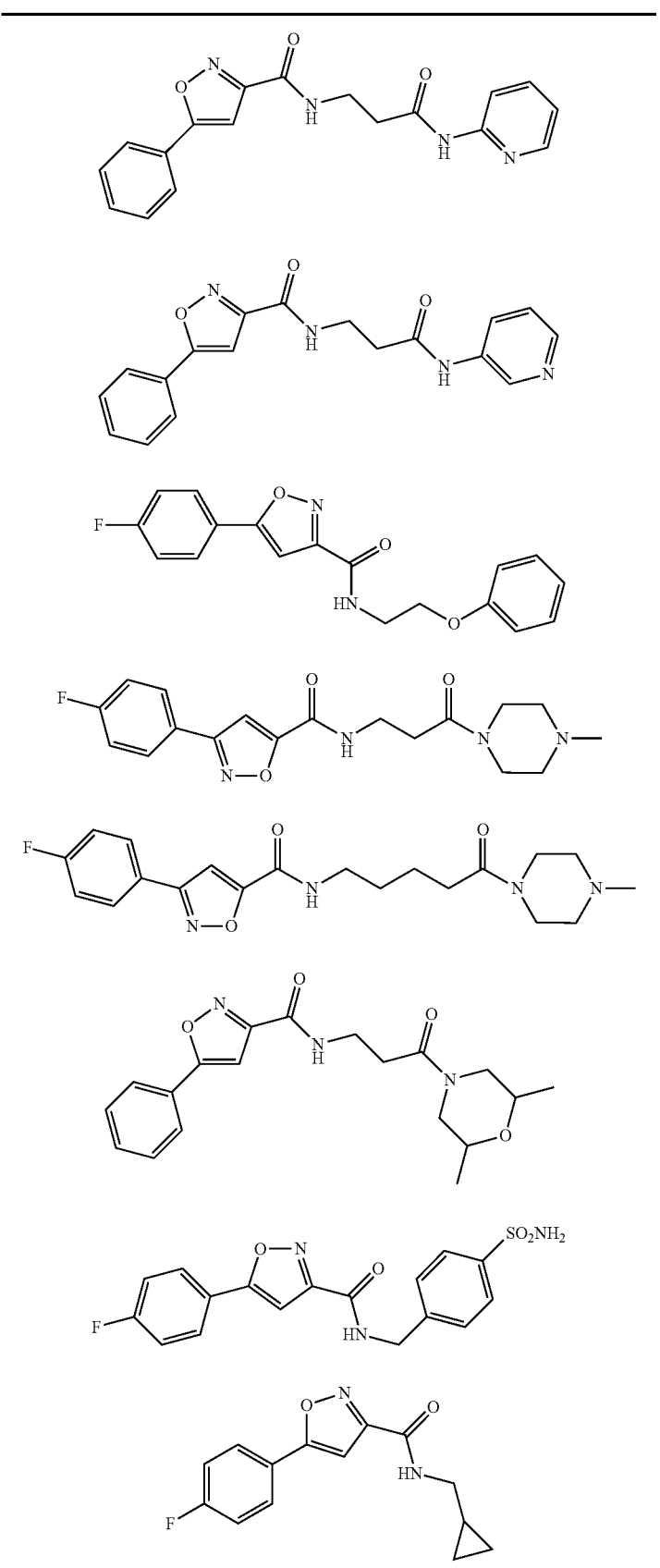

TABLE B-continued
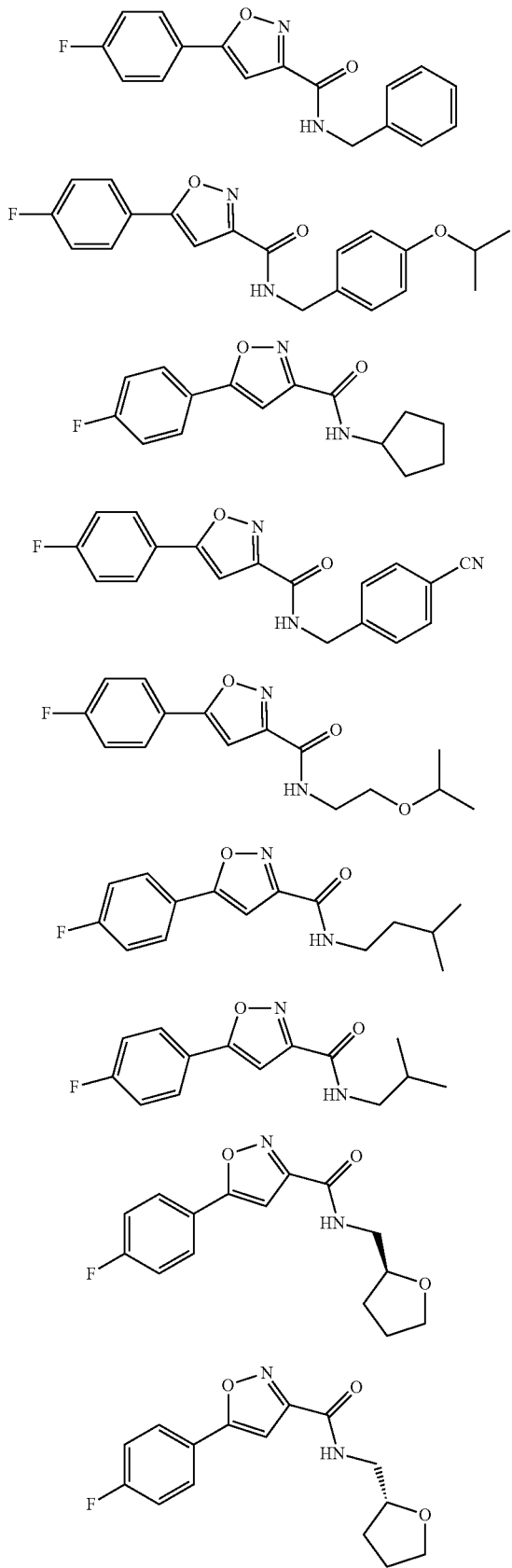

TABLE B-continued
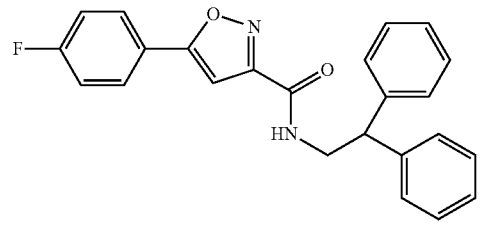 [SMILES: O=C(NCC(c1ccccc1)c1ccccc1)c1cc(-c2ccc(F)cc2)on1]
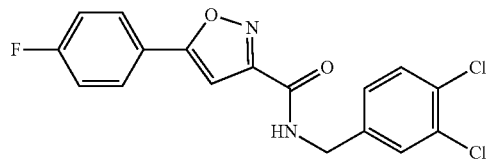 [SMILES: O=C(NCc1ccc(Cl)c(Cl)c1)c1cc(-c2ccc(F)cc2)on1]
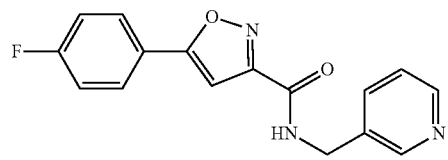 [SMILES: O=C(NCc1cccnc1)c1cc(-c2ccc(F)cc2)on1]
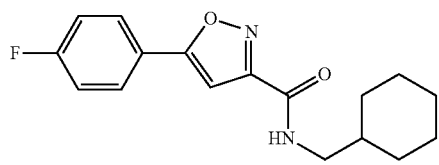 [SMILES: O=C(NCC1CCCCC1)c1cc(-c2ccc(F)cc2)on1]
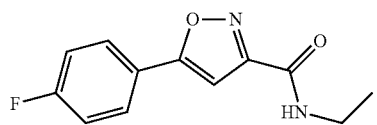 [SMILES: CCNC(=O)c1cc(-c2ccc(F)cc2)on1]
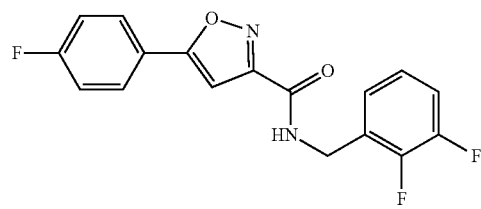 [SMILES: O=C(NCc1cccc(F)c1F)c1cc(-c2ccc(F)cc2)on1]
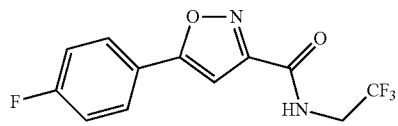 [SMILES: O=C(NCC(F)(F)F)c1cc(-c2ccc(F)cc2)on1]
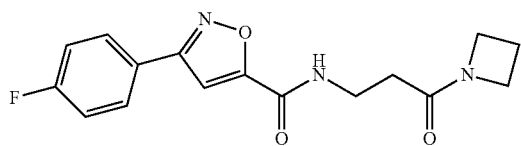 [SMILES: O=C(NCCC(=O)N1CCC1)c1cc(-c2ccc(F)cc2)no1]
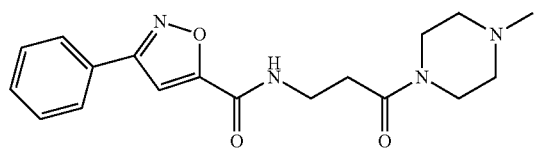 [SMILES: CN1CCN(C(=O)CCNC(=O)c2cc(-c3ccccc3)no2)CC1]

TABLE B-continued
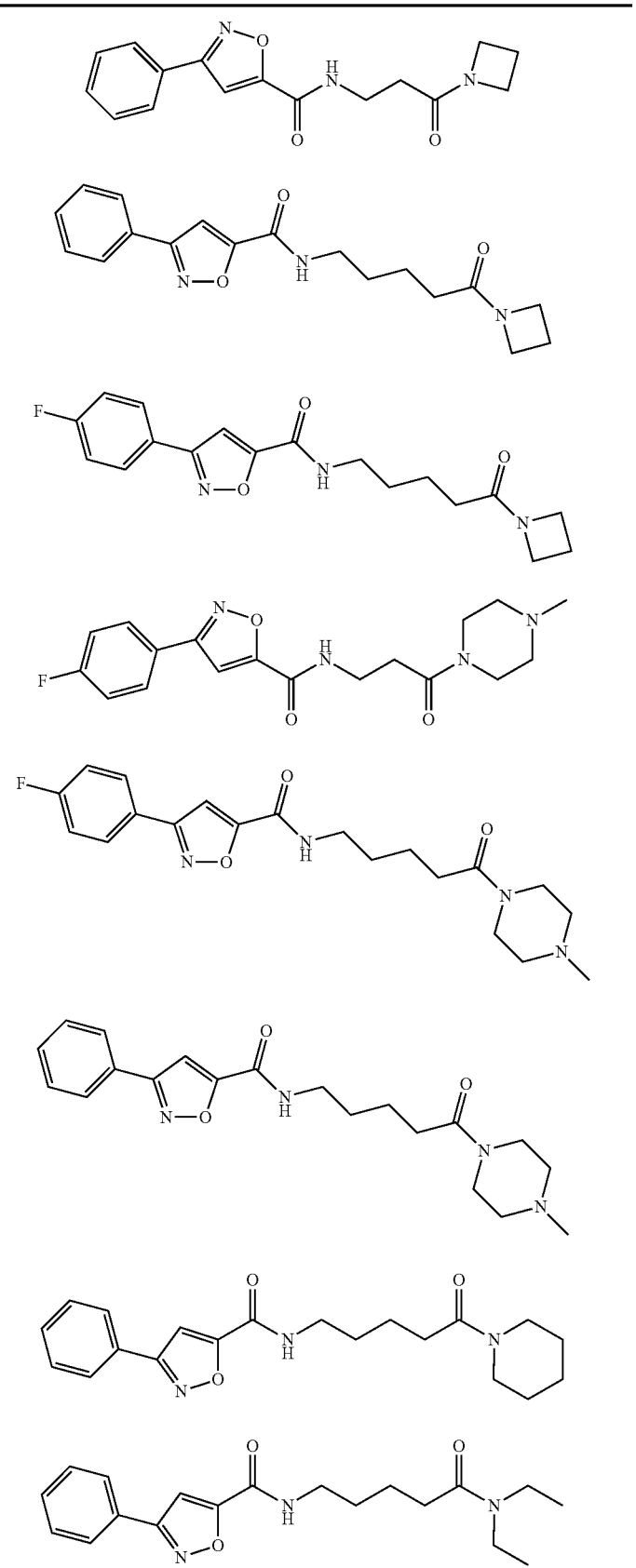

TABLE B-continued

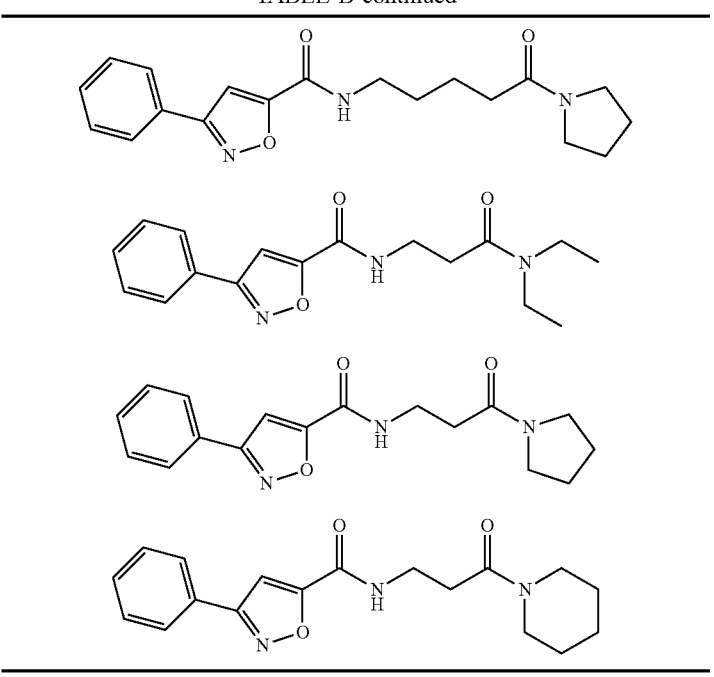

List Of Abbreviations:
All temperatures are in degrees Centigrade
CF—cystic fibrosis
CFTR—cystic fibrosis transmembrane conductance regulator
$CH_2Cl_2$—methylene chloride
DIPEA—N,N-diisopropylethylamine
DMF—dimethylformamide
DMSO—dimethylsulfoxide
ENaC—epithelial sodium channel
$Et_2O$—diethyl ether
$Et_3N$—triethylamine
EtOAc—ethyl acetate
h—hours
$H_2O$—water
HATU—(1-[Bis(dimethylamino)methylene]-1H-1,2,3-triazolo[4,5-b]pyridinium 3-oxid hexafluorophosphate)
HBS—Hepes-buffered saline
HCl—hydrochloric acid
HOAc—acetic acid
HPLC—high pressure liquid chromatography
hr—hours
HTS—high throughput screen
$Na_2SO_4$—sodium sulfate
NaH—sodium hydride
NaH—sodium hydride
$NaHCO_3$—sodium bicarbonate
NAUC—normalized area under the curve
$NH_4Cl$—ammonium chloride
NMR—nuclear magnetic resonance
PBS—Phosphate buffered saline
POCl3—phosphorus oxychloride
rt—room temperature
TFA—trifluoroacetic acid
THF—tetrahydrofuran
YFP—yellow fluorescent protein The compounds of this invention may be prepared by methods known in the art. Exemplary synthetic routes to prepare compounds of this invention are illustrated below:

Scheme I:

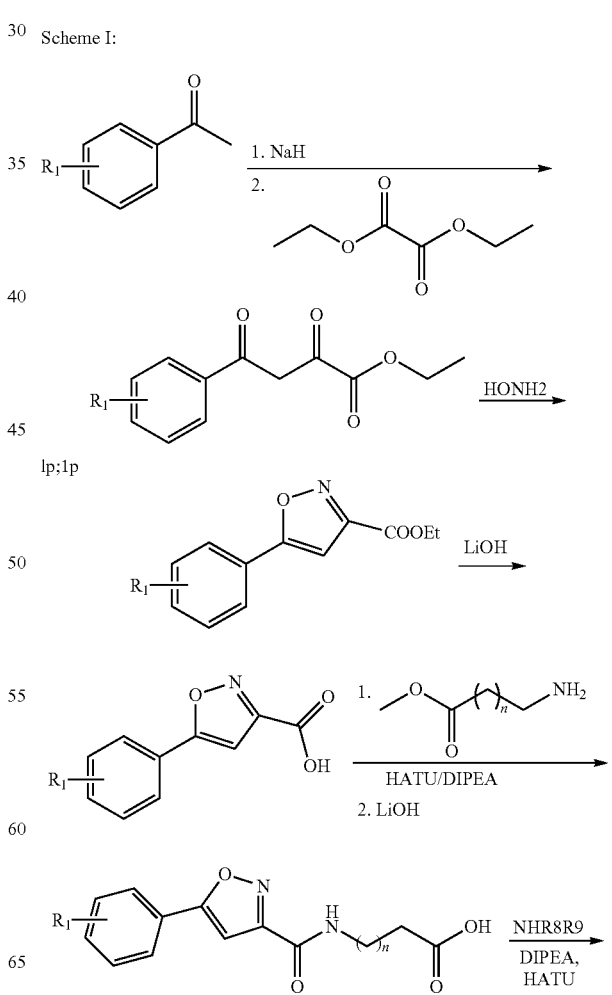

-continued

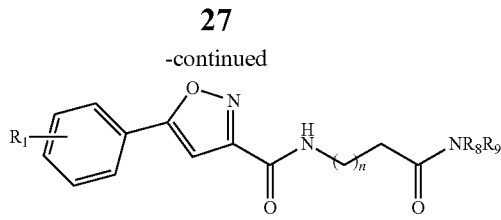

Scheme II:

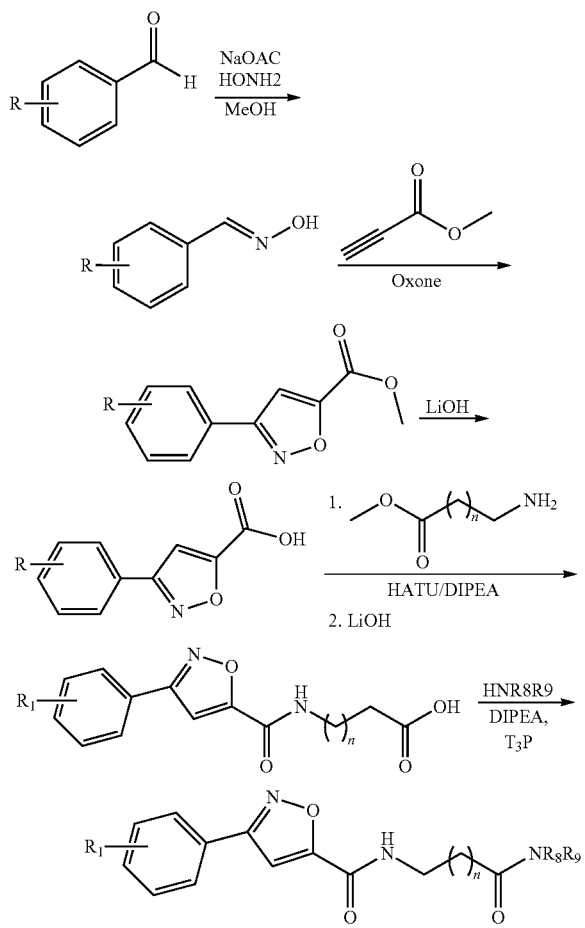

Scheme III:

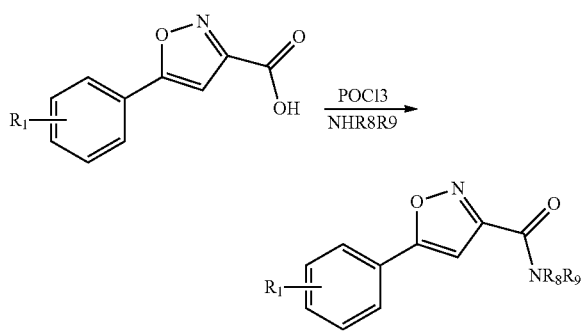

Scheme IV:

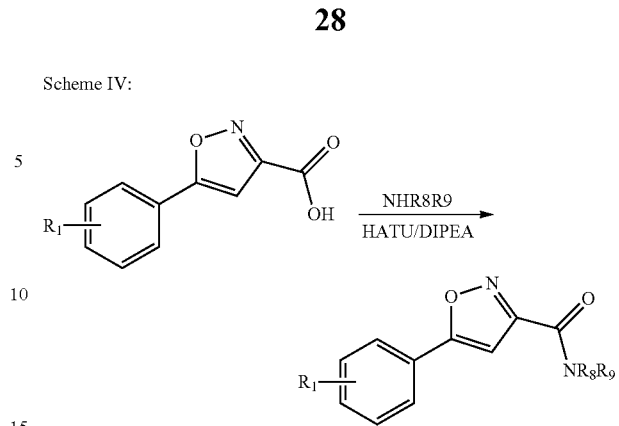

Compounds of the invention are useful as modulators of CFTR and treating diseases or disorders mediated by CFTR such as for the treatment of disease, disorders or conditions such as Cystic fibrosis, Asthma, Constipation, Pancreatitis, Gastrointestinal diseases or disorders, Infertility, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myeloperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington's disease, Spinocerebullar ataxia type I, Spinal and bulbar muscular atrophy, Dentororubal pallidoluysian, and Myotic dystrophy, as well as spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome, Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is oral administration.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The term parenteral as used herein includes subcutaneous, intracutaneous, intravenous, intramuscular, intraarticular, intraarterial, intrasynovial, intrasternal, intrathecal, intralesional and intracranial injection or infusion techniques.

In another embodiment, administration is parenteral administration by injection. Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

The compositions described herein can be formulated in a unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration. In one embodiment, the unit dosage form can have one of the compounds of the invention as an active ingredient in an amount of about 10 mg, 20 mg, 30 mg, 40 mg, 50 mg, 100 mg, 150 mg, 200 mg, 250 mg, 300 mg, 400 mg, 500 mg, 600 mg, 700 mg, 750 mg, 800 mg, 900 mg, 1000 mg, or 1,250 mg.

In some embodiments, the compounds of the invention can be administered in a dose of at least about 10 mg/day to at least about 1500 mg/day. In some embodiments, the compounds of the invention are administered in a dose of at least about 300 mg (e.g., at least about 450 mg, at least about 500 mg, at least about 750 mg, at least about 1,000 mg, at least about 1250 mg, or at least about 1500 mg).

Dose adjustments can be made for patients with mild, moderate or severe hepatic impairment (Child-Pugh Class A). Furthermore, dosage adjustments can be made for patients taking one or more Cytochrome P450 inhibitors and inducers, in particular CYP3A4, CYP2D6, CYP2C9, CYP2C19 and CYP2B6 inhibitors and inducers. Dose adjustments can also be made for patients with impaired Cytochrome P450 function such as poor, intermediate, extensive and ultra-rapid metabolizers.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1, 2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. CH$_3$—CH$_2$—), or in other instances, a bivalent linking moiety can be "alkyl," in which case those skilled in the art will understand the alkyl to be a divalent radical (e.g., —CH$_2$—CH$_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

The present invention includes all pharmaceutically acceptable isotopically-labeled or enriched compounds of the invention. The compounds include one or more atoms that are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, nitrogen, such as $^{13}$N and $^{15}$N, oxygen, such as $^{15}$O, $^{17}$O and $^{18}$O, chlorine, such as $^{36}$Cl, fluorine, such as $^{18}$F, iodine, $^{123}$I and $^{125}$I, phosphorus, such as $^{32}$P, and sulphur, such as $^{35}$S.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

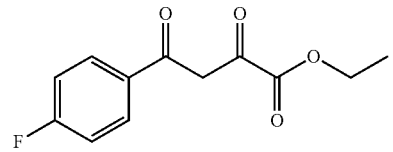 [SMILES: CCOC(=O)C(=O)CC(=O)c1ccc(F)cc1]

4-(4-fluorophenyl)-2,4-dioxobutanoate: To a stirred solution of NaH (60%) (15.0 g, 361 mmol), in toluene (400 mL) at 0° C., was added 4-fluoro acetophenone (25.0 g, 181 mmol) drop wise at 0° C. The reaction mixture was then stirred at 0° C. for 30 minutes. Diethyl oxalate (37 mL, 271 mmol) was added drop wise at 0° C. The reaction mixture was stirred at 25° C. for 2 h. The reaction mixture was diluted with water (1000 mL) and extracted in ethyl acetate (250 mL×3). The organic layer was washed with brine (250 mL), dried over anhydrous sodium sulphate and distilled off to obtain crude ethyl 4-(4-fluorophenyl)-2,4-dioxobutanoate (44.0 g) as a liquid. This was carry forward to next step without further purification. (238.96 [M+H]).

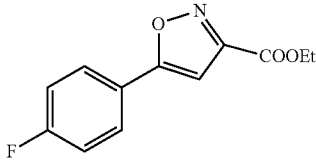 [SMILES: CCOC(=O)c1cc(-c2ccc(F)cc2)on1]

5-(4-fluorophenyl)isoxazole-3-carboxylate: To a stirred solution of ethyl 4-(4-fluorophenyl)-2,4-dioxobutanoate (44.0 g, 187 mmol) in ethanol (600 mL) at 0° C., was added hydroxyl amine hydrochloride (39.0 g, 561 mmol) portion wise at 0° C. The reaction mixture was then stirred at 80° C. for 3 h. The reaction mixture was concentrated under reduce pressure and the resulting residue was suspended in water (500 mL). The precipitates were collected by filtration and dried under vacuum to give crude product which was purified by column chromatography (eluted in 0-15% Ethyl acetate in Hexane) to obtained ethyl 5-(4-fluorophenyl) isoxazole-3-carboxylate (24.0 g, 236 [M+H]). 1H NMR: (400 MHz, DMSO) δ: 1.601-1.610 (t, 3H), 4.468-4.530 (m, 2H), 6.898-6.908 (t,1H), 7.188-7.230 (m, 2H), 7.810-7.849 (m, 2H).

5-(4-fluorophenyl)isoxazole-3-carboxylic acid: To a stirred solution of ethyl 5-(4-fluorophenyl)isoxazole-3-carboxylate (24.0 g, 100.8 mmol) in THF (150 mL) was added lithium hydroxide (16.5 g, 403 mmol) in water (150 mL). The reaction was stirred for 2 h. THF was distilled off the reaction mixture, water was added (300 mL), the solution was acidified with aq. 5N HCl (40 mL). The solid precipitate was collected and dried under vacuum to give 5-(4-fluorophenyl)isoxazole-3-carboxylic acid (18.0 g, 208 [M+H]) as a solid. $^1$H NMR: (400 MHz, DMSO) δ: 7.396-7.447 (m, 3H), 8.008-8.043 (m, 2H).

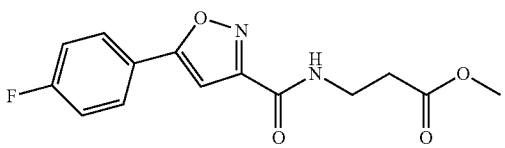 [SMILES: COC(=O)CCNC(=O)c1cc(-c2ccc(F)cc2)on1]

3-(5-(4-fluorophenyl)isoxazole-3-carboxamido)propanoate: To a stirred solution of 5-(4-fluorophenyl)isoxazole-3-carboxylic acid (2.0 g, 9.6 mmol) in DMF (20 mL) was added HATU (5.6 g, 14.4 mmol) at 0° C. The reaction mixture was then stirred at 0° C. for 30 minutes. Methyl 3-aminopropanoate hydrochloride (1.6 g, 11.5 mmol) was added portion wise and the reaction was stirred at 0° C. for 15 minutes. DIPEA (10 mL, 57.6 mmol) was added drop-wise 0° C. and the reaction mixture was stirred at 25° C. for 2 h. The reaction mixture was diluted with ice water (100 mL) and the resulting solid precipitate was filtered and dried under vacuum to obtained methyl 3-(5-(4-fluorophenyl) isoxazole-3-carboxamido)propanoate (1.84 g, 293 [M+H]) 1H NMR: (400 MHz, DMSO) δ: 2.602-2.637 (t, 2H), 3.485-3.534 (q, 2H), 3.615 (s, 3H), 7.378-7.388 (d, J=4, 1H), 7.396-7.441 (m, 2H), 7.996-8.031 (m, 2H), 8.880-8.907 (t,1H).

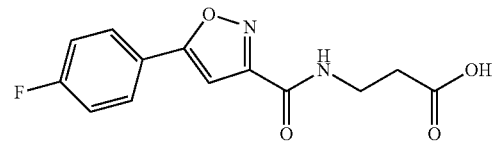 [SMILES: O=C(O)CCNC(=O)c1cc(-c2ccc(F)cc2)on1]

3-(5-(4-fluorophenyl)isoxazole-3-carboxamido)propanoic acid: To a stirred solution of methyl 3-(5-(4-fluorophenyl)isoxazole-3-carboxamido)propanoate (1.84 g, 6.3 mmol) in THF (20 mL) was added a solution of lithium hydroxide (1.03 g, 25.2 mmol) in water (20 mL). The reaction was stirred for 2 h. THF was distilled off, water (50 mL) was added, and the solution was acidified with aq. 5N.HCl (10 mL). The resulting solid precipitate was filtered and dried under vacuum to give 3-(5-(4-fluorophenyl)isoxazole-3-carboxamido)propanoic acid (1.18 g, 279 [M+H]). $^1$H NMR: (400 MHz, DMSO) δ: 2.503-2.557 (t, 2H), 3.454-3.503 (q 2H), 7.370-7.439 (m, 3H), 7.994-8.030 (dd, J=1.2, 3.6, 2H), 8.807-8.835 (t, 1H), 10.239 (s, 1H).

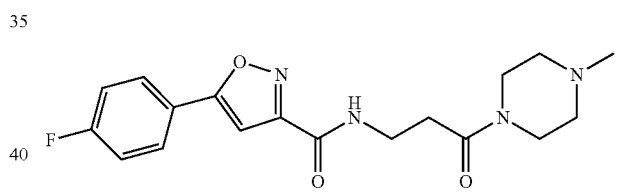

Example 1

5-(4-fluorophenyl)-N-(3-(4-methylpiperazin-1-yl)-3-oxopropyl)isoxazole-3-carboxamide: To a stirred solution of 3-(5-(4-fluorophenyl)isoxazole-3-carboxamido)propanoic acid (1.8 g, 6.47 mmol) in DMF (60 mL) was added HATU (3.69 g 9.7 mmol) at 0° C. The reaction mixture was stirred at 0° C. for 30 minute. Then 1-methylpiperazine (0.647 g, 6.47 mmol) was added and the reaction stirred for 10 minutes. Next DIPEA (3.5 mL, 19.4 mmol) was added drop-wise and the reaction was stirred at 25° C. for 1 h. Ice water was added and the mixture stirred for 30 minutes. The solid was filtered, washed with water and dried under vacuum to obtain 5-(4-fluorophenyl)-N-(3-(4-methylpiperazin-1-yl)-3-oxopropyl)isoxazole-3-carboxamide (1.10 g, 361 [M+H]). $^1$H NMR: (400 MHz, DMSO) (52204) δ: 2.170 (s, 3H), 2.228-2.303 (m, 4H), 2.598-2.634 (t, 2H), 3.416-3.505 (m, 6H), 7.375-7.439 (m, 3H), 7.996-8.031 (m, 2H), 8.698-8.727 (t, 1H).

Representative compounds of the invention are prepared similarly from 3-(5-(4-fluorophenyl)isoxazole-3-carboxamido)propanoic acid and the corresponding amine.

| Example | LC/MS m/z |
|---|---|
| 2. 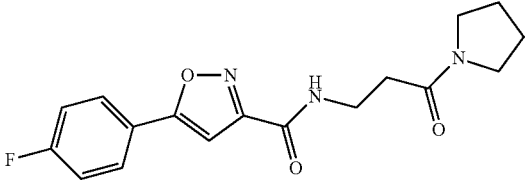 [SMILES: O=C(NCCC(=O)N1CCCC1)c1cc(-c2ccc(F)cc2)on1] | 332 [M + H] |
| 3. 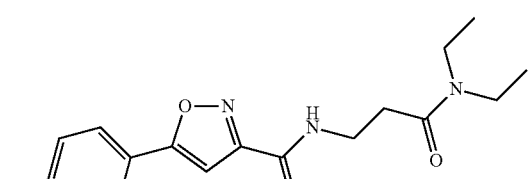 | 334 [M + H] |
| 4. 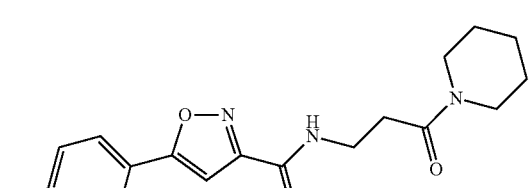 | 346 [M + H] |
| 5. 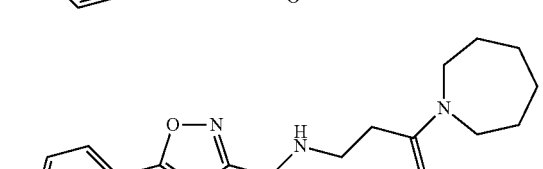 | 360 [M + H] |
| 6. 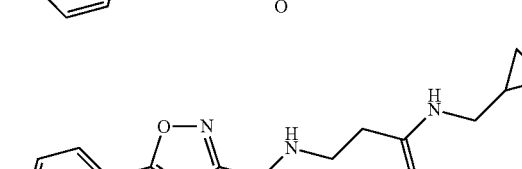 | 332 [M + H] |
| 7. 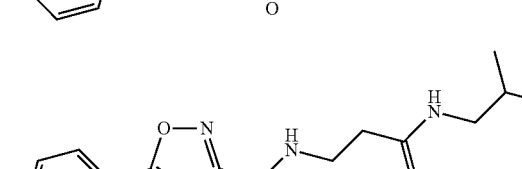 | 334 [M + H] |
| 8. 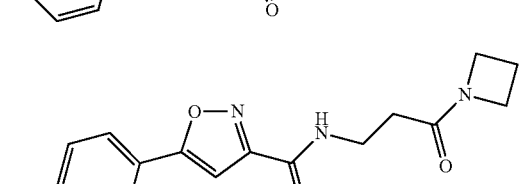 | 318 [M + H] |
| 9. 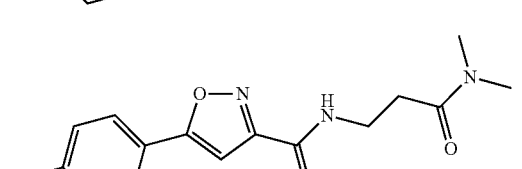 | 306 [M + H] |

| Example | LC/MS m/z |
|---|---|
| 10. | 348 [M + H] |
| 11. | 336 [M + H] |
| 12. | 368 [M + H] |
| 13. | 355 [M + H] |

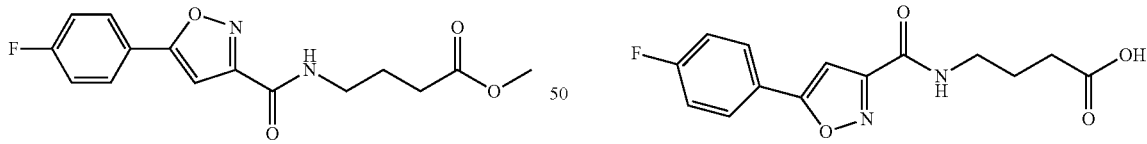

4-(5-(4-fluorophenyl)isoxazole-3-carboxamido)butanoate: To a stirred solution of 5-(4-fluorophenyl)isoxazole-3-carboxylic acid (0.2 g, 0.96 mmol) in DMF (8 mL) was added HATU (0.548 g, 1.44 mmol) at 0° C. The reaction mixture was then stirred at 0° C. for 30 minutes and methyl 4-aminobutanoate hydrochloride (0.148 g, 0.96 mmol) was added portion wise at 0° C. and stirred for 15 minutes. DIPEA (0.49 mL, 2.88 mmol) was added drop wise at 0° C. The reaction mixture was stirred at 25° C. for 2 h. The reaction was quenched in ice water (30 mL) and the mixture was stirred for 30 min. The solid precipitate was filtered and dried under vacuum to give methyl 4-(5-(4-fluorophenyl) isoxazole-3-carboxamido)butanoate (0.100 g, 307 [M+H]).

4-(5-(4-fluorophenyl)isoxazole-3-carboxamido)butanoic acid: To a stirred solution of methyl 4-(5-(4-fluorophenyl) isoxazole-3-carboxamido)butanoate (0.100 g, 0.32 mmol) in THF (5 mL) was added lithium hydroxide (0.054 g, 1.3 mmol) in water (5 mL). The reaction was stirred for 2 h. THF was distilled off, water (10 mL) was added, and the solution was acidified with aq. 5N HCl (4 mL). The resulting solid precipitate was filtered and dried under vacuum to give 4-(5-(4-fluorophenyl)isoxazole-3-carboxamido)butanoic acid (0.075 g, 293[M+H])) $^1$H NMR: (400 MHz, DMSO) δ: 1.921-1.957 (q 2H), 2.398-2.434 (q, 2H), 3.447-3.482 (q, 2H), 7.076 (s, 1H), 7.277-7.321 (m, 2H), 7.931-7.967 (m, 2H).

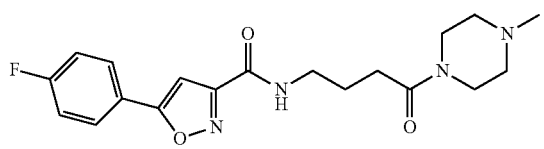 [SMILES: CN1CCN(C(=O)CCCNC(=O)c2cc(-c3ccc(F)cc3)on2)CC1]

Example 14

5-(4-fluorophenyl)-N-(4-(4-methylpiperazin-1-yl)-4-oxobutyl)isoxazole-3-carboxamide: To a stirred solution of 5-(4-fluorophenyl)isoxazole-3-carboxylic acid (0.075 g, 0.25 mmol) in DMF (6 mL) was added HATU (0.145 g, 0.384 mmol) at 0° C. The reaction mixture was then stirred at 0° C. for 30 minutes. Then 1-methylpiperazine (0.03 mL, 0.25 mmol) was added portion wise at 0° C. and stirred for 15 minutes. Next, DIPEA (0.13 mL, 0.77 mmol) was added drop wise at 0° C. The reaction mixture was stirred at 25° C. for 2 h. The reaction was quenched in ice water (20 mL) and the resulting mixture was stirred for 30 min. The solid precipitate was filtered and dried under vacuum to give 5-(4-fluorophenyl)-N-(4-(4-methylpiperazin-1-yl)-4-oxobutyl)isoxazole-3-carboxamide (0.095 g, 375 [M+H])) $^1$H NMR: (400 MHz, DMSO) δ: 2.171 (s, 3H), 2.212-2.237 (t, 2H), 2.272-2.296 (t, 2H), 2.344-2.380 (t, 2H), 3.262-3.294 (q, 2H), 3.400-3.435 (q, 4H), 7.362 (s, 1H), 7.397-7.441 (m, 2H), 7.992-8.028 (m, 2H), 8.829-8.857 (t,1H).

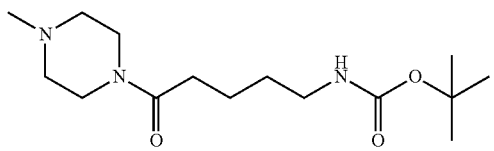 [SMILES: CN1CCN(C(=O)CCCCNC(=O)OC(C)(C)C)CC1]

tert-butyl (5-(4-methylpiperazin-1-yl)-5-oxopentyl) carbamate: To a stirred solution of 5-((tert-butoxycarbonyl)amino)pentatonic acid (1.08 g, 4.99 mmol) in DMF (10 mL) at 0° C. was added HATU (2.85 g, 7.48 mmol) and the resulting reaction mixture was stirred at 0° C. for 30 minutes. Next, 1-methylpiperazine (0.5 g, 4.99 mmol) was added at 0° C. and stirred for 5 minutes at 0° C. Then DIPEA (2.58 mL, 14.97 mmol) was added drop wise at 0° C. and the reaction mixture was stirred at 25° C. for 1 h. The reaction mixture was diluted with water (50 mL) and extracted in EtOAc (25 mL×2). The organic layer was washed with brine (50 mL), dried over anhydrous sodium sulfate and distilled off to give crude product which was purified by column chromatography (0.5% methanol in dichloromethane) to obtained tert-butyl (5-(4-methylpiperazin-1-yl)-5-oxopentyl) carbamate (0.833 g, 300 [M+1]).

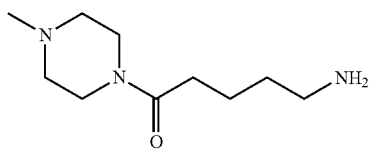

5-amino-1-(4-methylpiperazin-1-yl)pentan-1-one: To a stirred solution of tert-butyl (5-(4-methylpiperazin-1-yl)-5-oxopentyl) carbamate (1 g, 3.3 mmol) in dichloromethane (10 mL) at 0° C. was added TFA (1.27 mL, 16.6 mmol) drop wise. The reaction warmed to rt and stirred for 3 h. Solvent was distilled off to give crude product 5-amino-1-(4-methylpiperazin-1-yl)pentan-1-one (2.0 g, 200 [M+H]) which was carried forward to the next step without purification.

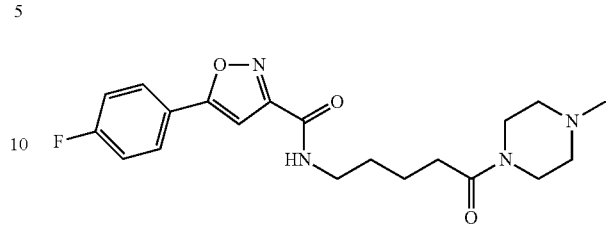

Example 15

5-(4-fluorophenyl)-N-(5-(4-methylpiperazin-1-yl)-5-oxopentyl)isoxazole-3-carboxamide: To a stirred solution of 5-(4-fluorophenyl)isoxazole-3-carboxylic acid (0.3 g, 1.44 mmol) in DMF (15 mL) at 0° C. was added HATU (0.825 g, 2.17 mmol) at 0° C. and reaction mixture was stirred for 30 minutes. After 30 minutes, 5-amino-1-(4-methylpiperazin-1-yl)pentan-1-one (0.289 g, 1.44 mmol) was added at 0° C. and the reaction was stirred for 5 minutes at 0° C. Next, DIPEA (1.24 mL, 7.2 mmol) was added drop wise at 0° C. and the reaction mixture was stirred at 25° C. for 1 h. The reaction mixture was diluted with water (50 mL) and extracted in EtOAc (25 mL×2). The organic layer was washed with brine (50 mL), dried over anhydrous sodium sulfate and distilled off to give crude product which was purified by prep HPLC to obtained 5-(4-fluorophenyl)-N-(5-(4-methylpiperazin-1-yl)-5-oxopentyl)isoxazole-3-carboxamide (0.095 g, 389 [M+1]), 1H NMR: (400 MHz, DMSO) δ: 1.507-1.542 (m, 4H), 2.164 (s, 3H), 2.209-2.233 (m, 2H), 2.265-2.287 (m, 2H), 2.313-2.347 (m, 2H), 3.245-3.275 (m, 2H), 3.423 (s, 4H), 7.356 (s, 1H), 7.395-7.440 (m, 2H), 7.992-8.027 (m, 2H), 8.816-8.844 (d, 5.6 Hz, 1H).

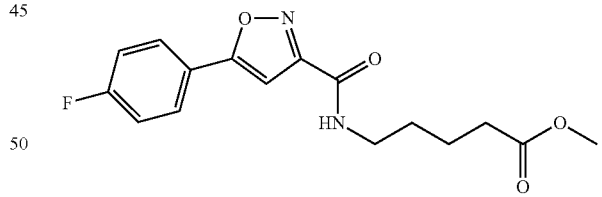

5-(5-(4-fluorophenyl)isoxazole-3-carboxamido)pentanoate: To a stirred solution of 5-(4-fluorophenyl)isoxazole-3-carboxylic acid (4.0 g, 19.3 mmol) in DMF (40 mL) was added HATU (11.0 g, 28.9 mmol) at 0° C. and the solution was stirred for 30 minutes. Methyl 5-aminopentanoate hydrochloride (5.8 g, 35 mmol) was added portion wise and the reaction was stirred 15 minutes. DIPEA (19.9 mL, 115 mmol) was added drop wise and the reaction stirred at 25° C. for 2 h. The reaction mixture was diluted with ice water (300 mL) and the solid precipitate was filtered and dried under vacuum to obtained methyl 5-(5-(4-fluorophenyl)isoxazole-3-carboxamido)pentanoate (9.0 g, 321 [M+H]).

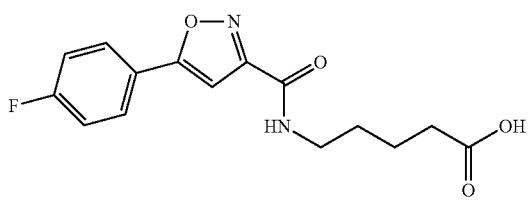 [SMILES: O=C(O)CCCCNC(=O)c1cc(-c2ccc(F)cc2)on1]

5-(5-(4-fluorophenyl)isoxazole-3-carboxamido)pentanoic acid: To a stirred solution of methyl 5-(5-(4-fluorophenyl)isoxazole-3-carboxamido)pentanoate (9 g, 28.17 mmol) in THF (100 mL) was added lithium hydroxide (4.6 g, 112 mmol) in water (100 mL). The reaction was stirred for 2 h. THF was distilled off and water was added (250 mL), acidified with aq. 5N HCl (30 mL). The precipitate was filtered and dried under vacuum to give 5-(5-(4-fluorophenyl)isoxazole-3-carboxamido)pentanoic acid (6.3 g, 307 [M+H]) $^1$H NMR: (400 MHz, DMSO) δ: 1.535 (s, 4H), 2.250 (s, 2H), 3.253-3.349 (d, J=6, 2H), 7.359-7.437 (m,3H), 7.991-8.026 (m, 2H), 8.835-8.863 (t, 2H), 12.050 (s,1H).

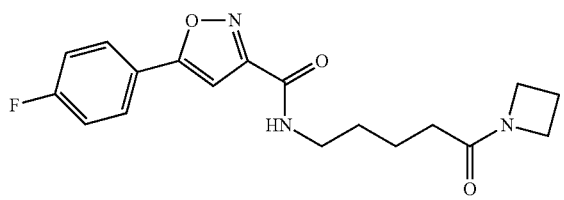 [SMILES: O=C(NCCCCC(=O)N1CCC1)c1cc(-c2ccc(F)cc2)on1]

Example 16

N-(5-(azetidin-1-yl)-5-oxopentyl)-5-(4-fluorophenyl)isoxazole-3-carboxamide: To a stirred solution of 5-(5-(4-fluorophenyl)isoxazole-3-carboxamido)pentanoic acid (6.3 g, 20.5 mmol) in DMF (60 mL) was added HATU (11.68 g, 30.7 mmol) at 0° C. and the solution stirred for 30 minutes. Azitidine HCl (2.3 g, 24.6 mmol) was added portion wise and mixture stirred for 15 minutes. DIPEA (22 mL, 123 mmol) was added drop wise and reaction stirred at 25° C. for 2 h. The reaction mixture was diluted with ice water (300 mL) and the solid precipitate was filtered and dried under vacuum to give crude product which was purified by column chromatography (0-5% methanol in dichloromethane) to obtained N-(5-(azetidin-1-yl)-5-oxopentyl)-5-(4-fluorophenyl)isoxazole-3-carboxamide (4.5 g, 346 [M+H]). $^1$H NMR (400 MHz, DMSO) δ: 1.480-1.515 (m, 4H), 2.019-2.054 (t, 2H), 2.122-2.199 (q, 2H), 3.228-3.259 (m, 2H), 3.792-3.830 (m, 2H), 4.072-4.110 (m, 2H), 7.361 (S,1H), 7.396-7.441 (m, 2H), 7.993-8.029 (m, 2H), 8.8824-8.853 (t, 1H).

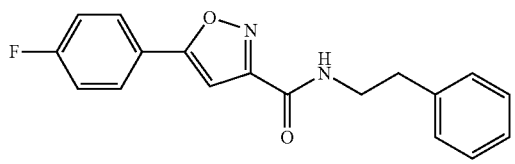 [SMILES: O=C(NCCc1ccccc1)c1cc(-c2ccc(F)cc2)on1]

Example 17

5-(4-fluorophenyl)-N-phenethylisoxazole-3-carboxamide: To a stirred solution of 5-(4-fluorophenyl)isoxazole-3-carboxylic acid (0.2 g, 0.96 mmol) in DMF (8 mL) was added HATU (0.55 g 1.44 mmol) at 0° C. and the reaction mixture was stirred at 0° C. for 30 minutes. Next, phenylethan-1-amine (0.120 g, 0.96 mmol) was added and the reaction stirred for 10 minute at 0° C. Then DIPEA (0.5 mL, 2.8 mmol) was added drop wise and the reaction was stirred at 25° C. for 1 h. The reaction mixture was quench in ice cold water and the resulting solid mass was filter out. The crude product was purified by column chromatography (10-15% ethyl acetate in hexane) to give 5-(4-fluorophenyl)-N-phenethylisoxazole-3-carboxamide (0.110 g, 311 [M+H]), $^1$H NMR: (400 MHz, DMSO) δ: 2.843-2.881 (m, 2H), 3.477-3.529 (m, 2H), 7.195-7.3.327 (m, 5H), 7.354 (m, 1H), 7.397-7.442 (m, 2H), 7.995-8.030 (dd, J=9.2, 6.4, 2H), 8.895-8.924 (t,1H).

Representative compounds of the invention are prepared similarly from 5-(4-fluorophenyl)isoxazole-3-carboxylic acid and the corresponding amine.

| Example | | LC/MS m/z |
|---|---|---|
| 18. | ![structure] | 376 [M + H] |
| 19. | ![structure] | 355 [M + H] |
| 20. | ![structure] | 293 [M + H] |

-continued
| Example | LC/MS m/z |
|---|---|
| 21. 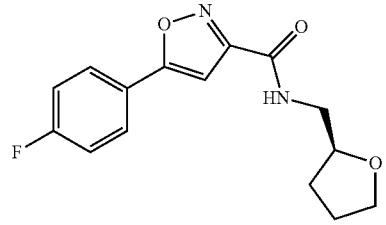 [SMILES: O=C(NC[C@@H]1CCCO1)c1cc(-c2ccc(F)cc2)on1] | 291 [M + H] |
| 22. 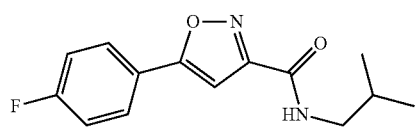 [SMILES: CC(C)CNC(=O)c1cc(-c2ccc(F)cc2)on1] | 263 [M + H] |
| 23. 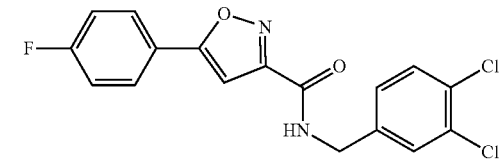 [SMILES: O=C(NCc1ccc(Cl)c(Cl)c1)c1cc(-c2ccc(F)cc2)on1] | 366 [M + H] |
| 24. 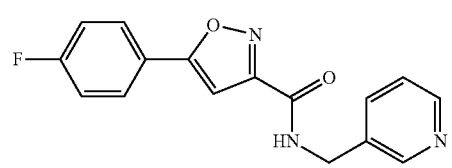 [SMILES: O=C(NCc1cccnc1)c1cc(-c2ccc(F)cc2)on1] | 298 [M + H] |
| 25. 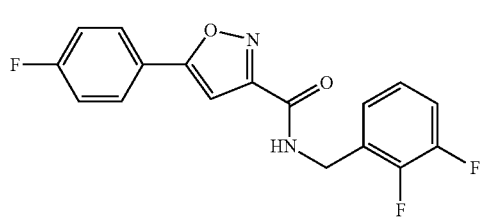 [SMILES: O=C(NCc1cccc(F)c1F)c1cc(-c2ccc(F)cc2)on1] | 333 [M + H] |
| 26. 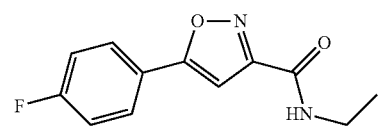 [SMILES: CCNC(=O)c1cc(-c2ccc(F)cc2)on1] | 235 [M + H] |
| 27. 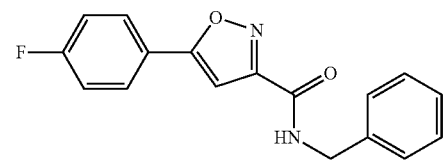 [SMILES: O=C(NCc1ccccc1)c1cc(-c2ccc(F)cc2)on1] | 297 [M + H] |
| 28. 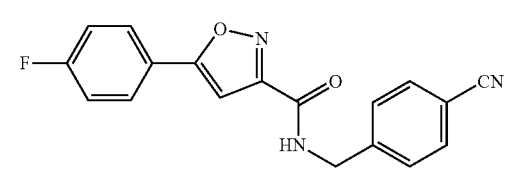 [SMILES: N#Cc1ccc(CNC(=O)c2cc(-c3ccc(F)cc3)on2)cc1] | 322 [M + H] |
| 29. 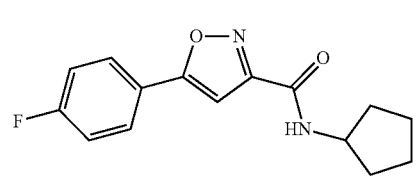 [SMILES: O=C(NC1CCCC1)c1cc(-c2ccc(F)cc2)on1] | 275 [M + H] |

-continued

| Example | | LC/MS m/z |
|---|---|---|
| 30. | 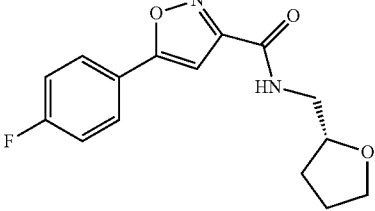 | 291 [M + H] |
| 31. | 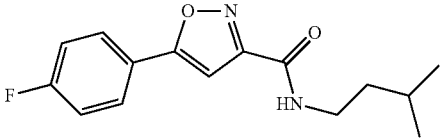 [SMILES: CC(C)CCNC(=O)c1cc(-c2ccc(F)cc2)on1] | 277 [M + H] |
| 32. | 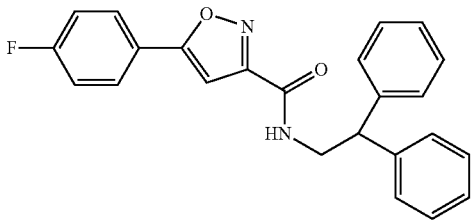 [SMILES: O=C(NCC(c1ccccc1)c1ccccc1)c1cc(-c2ccc(F)cc2)on1] | 387 [M + H] |
| 33. | 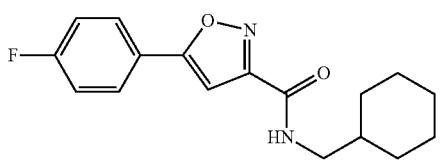 [SMILES: O=C(NCC1CCCCC1)c1cc(-c2ccc(F)cc2)on1] | 303 [M + H] |
| 34. | 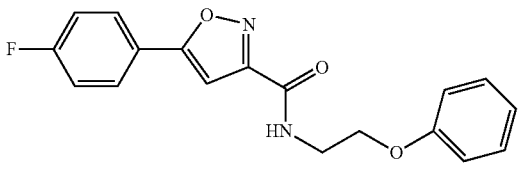 [SMILES: O=C(NCCOc1ccccc1)c1cc(-c2ccc(F)cc2)on1] | 327 [M + H] |
| 35. | 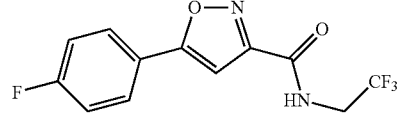 [SMILES: O=C(NCC(F)(F)F)c1cc(-c2ccc(F)cc2)on1] | 289 [M + H] |

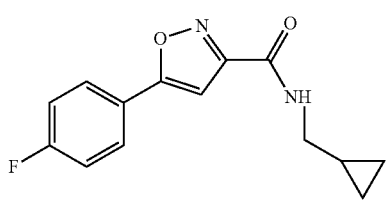 [SMILES: O=C(NCC1CC1)c1cc(-c2ccc(F)cc2)on1]

Example 36

N-(cyclopropylmethyl)-5-(4-fluorophenyl)isoxazole-3-carboxamide: A stirred solution of 5-(4-fluorophenyl)isoxazole-3-carboxylic acid (0.1 g, 0.48 mmol) and cyclopropylmethanamine (0.034 g, 0.48 mmol) in dichloromethane (5 mL) was cooled to 0° C. Pyridine (0.2 mL) was added and the reaction stirred for 10 minutes. Then POCl3 (0.2 mL) was added drop wise and reaction mixture was stirred for 1 h at 25° C. Ice water was added and the product was extracted into dichloromethane (2×25 ml). The organic layer was washed with saturated NaHCO3 (25 ml), brine, dried over Na2SO4 and concentrated to obtained crude product which was purified by column purification (0-20% ethyl acetate in hexane) to obtained N-(cyclopropylmethyl)-5-(4-fluorophenyl)isoxazole-3-carboxamide (0.057 g, 261 [M+H]); $^1$H NMR: (400 MHz, DMSO) δ: 0.256-0.270 (q, 2H), 0.422-0.467 (m, 2H), 1.033-1.070 (m, 1H), 3.128-3.160 (t, 2H), 7.370-7.442 (m, 3H), 7.997-8.032 (m, 2H) 8.896-8.925 (t, 1H).

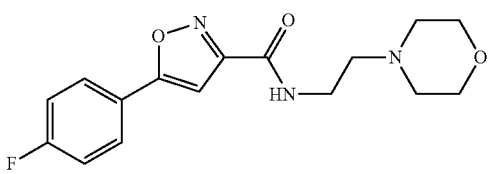 [SMILES: O=C(NCCN1CCOCC1)c1cc(-c2ccc(F)cc2)on1]

Example 37

5-(4-fluorophenyl)-N-(2-morpholinoethyl)isoxazole-3-carboxamide: A stirred solution of 5-(4-fluorophenyl)isoxazole-3-carboxylic acid (0.1 g, 0.48 mmol) and 2-morpholinoethan-1-amine (0.127 g, 0.97 mmol) in dichloromethane (5 mL) was cooled to 0° C. Pyridine (0.2 mL) was added and the reaction stirred for 10 minutes. POCl3 (0.2 mL) was added drop wise and the reaction mixture was stirred for 1 h at 25° C. Ice water was added and the product was extracted into dichloromethane (2×25 ml). The organic layer was washed with saturated NaHCO3 (25 ml), brine, dried over Na2SO4 and concentrated to obtained crude product which was purified by flash column chromatography (0-20% ethyl acetate in hexane) to obtained 5-(4-fluorophenyl)-N-(2-morpholinoethyl)isoxazole-3-carboxamide (0.090 g, 319 [M+H]). 1H NMR: (400 MHz, DMSO) δ: 2.420 (s, 4H), 2.462-2.479 (m, 2H), 3.374-3.423 (m, 2H), 3.563-3.585 (t, J=4.4, 4H), 7.365 (s, 1H), 7.397-7.442 (t, J=8.8, 2H), 7.998-8.033 (m, 2H), 8.671-8.699 (t, J=5.6, 1H).

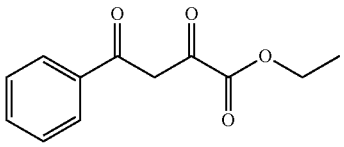 [SMILES: CCOC(=O)C(=O)CC(=O)c1ccccc1]

Ethyl 2,4-dioxo-4-phenylbutanoate: To a stirred solution of NaH (60%) (17.0 g, 418 mmol), in toluene (400 mL) at 0° C., was added acetophenone (25.0 g, 208 mmol) drop wise at 0° C. The reaction mixture was then stirred at 0° C. for 30 minutes. Diethyl oxalate (43 mL, 312 mmol) was then added drop wise at 0° C. The reaction mixture was stirred at 25° C. for 2 h. The reaction mixture was diluted with water (1000 mL) and extracted in ethyl acetate (3×250 mL). The organic layer was washed with brine (250 mL), dried over anhydrous sodium sulphate and distilled off to obtain crude ethyl 2,4-dioxo-4-phenylbutanoate (48.0 g, 221 [M+H]) as a liquid. This material was carried forward to next step without further purification.

Ethyl 5-phenylisoxazole-3-carboxylate: To a stirred solution of ethyl 2,4-dioxo-4-phenylbutanoate (48.0 g, 218 mmol) in ethanol (600 mL) at 0° C., was added hydroxyl amine hydrochloride (46.0 g, 654 mmol) portion wise. The mixture was then stirred at 80° C. for 3 h. The reaction mixture was concentrated under reduce pressure and the resulting residue was suspended in water (500 mL). The precipitate was collected by filtration and dried under vacuum to give crude product which was purified by column chromatography (0-7% Ethyl acetate in hexane) to obtained ethyl 5-phenylisoxazole-3-carboxylate (28.0 g, 218 [M+H]).

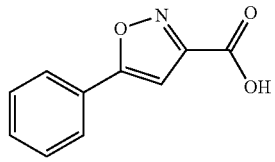 [SMILES: O=C(O)c1cc(-c2ccccc2)on1]

5-phenylisoxazole-3-carboxylic acid: To a stirred solution of ethyl 5-phenylisoxazole-3-carboxylate (28.0 g, 129 mmol) in THF (200 mL) was added lithium hydroxide (21.16 g, 516 mmol) in water (200 mL). The reaction was stirred for 2 h. The organic solvent was distilled off, water was added (500 mL), and acidified with aq. 5N HCl (50 mL). The solid precipitate was collected by filtration and dried under vacuum to give 5-phenylisoxazole-3-carboxylic acid (24.0 g, 190 [M+H]); 1H NMR: (400 MHz, DMSO) δ: 7.438 (S,1H), 7.524-7.593 (m,3H), 7.945-7.969 (m, 2H), 14.115 (S, 1H).

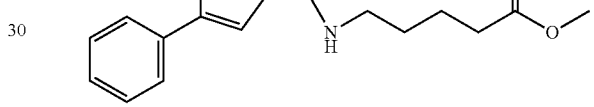

5-(5-phenylisoxazole-3-carboxamido)pentanoate: To a stirred solution of 5-aminopentanoic acid (7.35 g, 59.8 mmol) in methanol (50 mL) was added thionyl chloride (4.9 mL, 65.8 mmol) drop wise at 0° C. The reaction was stirred at 25° C. for 16 h. The reaction mixture was concentrated under reduce pressure and the resulting residue was suspended in diethyl ether (100 mL). The solid precipitate was collected by filtration and dried under vacuum to obtain methyl 5-aminopentanoate hydrochloride. To a stirred solution of 5-phenylisoxazole-3-carboxylic acid (7.4 g, 39.1 mmol) in DMF (80 mL) was added HATU (22.3 g, 58.6 mmol) at 0° C. and the reaction mixture was then stirred at 0° C. for 30 minutes. Methyl 5-aminopentanoate hydrochloride (7.8 g, 46.9 mmol) was added portion wise and the reaction mixture was stirred for 15 minutes. DIPEA (34.0 mL, 195 mmol) was added drop wise and the reaction mixture was stirred at 25° C. for 2 h. Reaction mixture was diluted with ice water (500 mL) and the solid precipitate was collected by filtration and dried under vacuum to obtained methyl 5-(5-phenylisoxazole-3-carboxamido)pentanoate (9.5 g, 279 [M+H]); 1H NMR: (400 MHz, DMSO) δ: 1.545-1.580 (m, 4H), 2.336-2.371 (m, 2H), 3.243-3.289 (d, J=12.4, 2H), 3.589 (S, 3H), 7.364 (S,1H), 7.538-7.581 (m, 3H), 7.927-7.951 (dd, J=1.6, 7.2, 2H), 8.836-8.865 (t,1H).

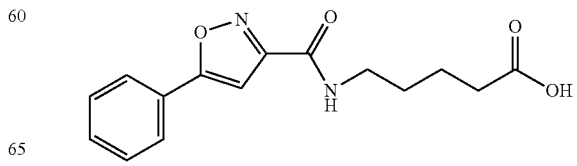

5-(5-phenylisoxazole-3-carboxamido)pentanoic acid: To a stirred solution of methyl 5-(5-phenylisoxazole-3-carboxamido)pentanoate (9.5 g, 31.4 mmol) in THF (100 mL) was added lithium hydroxide (5.2 g, 125.9 mmol) in water (100 mL). The reaction was stirred for 2 h. The organic solvent was distilled off, water was added (250 mL), and acidified with aq. 5N HCl (20 mL). The solid precipitate was collected by filtration and dried under vacuum to give 5-(5-phenylisoxazole-3-carboxamido)pentanoic acid (7.0 g, 289 [M+H]); $^1$H NMR: (400 MHz, DMSO) δ: 1.539 (s, 4H), 2.236-2.270 (m, 2H), 3.257-3.272 (d, J=6.0, 2H), 7.366 (S,1H), 7.541-7.590 (m, 3H), 7.926-7.950 (dd, J=2.0, 7.2, 2H), 8.842-8.871 (t,1H), 12.056 (s,1H).

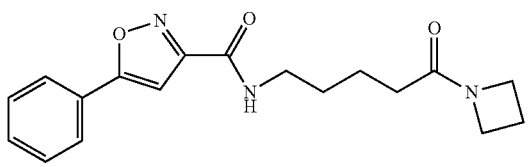 [SMILES: O=C(NCCCCC(=O)N1CCC1)c1cc(-c2ccccc2)on1]

portion wise and stirred for 15 minutes. DIPEA (21.0 mL, 121.5 mmol) was added drop wise and the reaction mixture was stirred at 25° C. for 2 h. The reaction mixture was diluted with water (250 mL) and extracted in ethyl acetate (3×100 mL). The organic layer was washed with brine (100 mL), dried over anhydrous sodium sulphate and distilled off to obtain crude product which was purified by column chromatography (0-5% methanol in dichloromethane) to give a solid product. The solid product was triturated with diethyl ether and pentane to obtain N-(5-(azetidin-1-yl)-5-oxopentyl)-5-phenylisoxazole-3-carboxamide (4.3 g, 328 [M+H]). 1H NMR (400 MHz, DMSO) δ: 1.481-1.517 (m, 4H), 2.020-2.055 (t, 2H), 2.120-2.197 (qt, 2H), 3.232-3.278 (m,2H), 3.791-3.830 (m,2H), 4.071-4.109 (m,2H), 7.369 (S,1H), 7.537-7.590 (m, 3H), 7.928-7.952 (dd, J=2.0, 3.6 2H), 8.835-8.864 (t,1H).

Representative compounds of the invention are prepared similarly from 5-(5-phenylisoxazole-3-carboxamido)pentanoic acid and the corresponding amine.

| Example | | LC/MS m/z |
|---|---|---|
| 39. | ![structure] | 342 [M + H] |
| 40. | ![structure] | 365 [M + H] |
| 41. | ![structure] | 365 [M + H] |
| 42. | ![structure] | 365 [M + H] |

Example 38

N-(5-(azetidin-1-yl)-5-oxopentyl)-5-phenylisoxazole-3-carboxamide: To a stirred solution of 5-(5-phenylisoxazole-3-carboxamido)pentanoic acid (7.0 g, 24.3 mmol) in DMF (70 mL) was added HATU (14.0 g, 36.4 mmol) at 0° C. The reaction mixture was then stirred at 0° C. for 30 minutes. Azetidine hydrochloride (2.8 g, 29.2 mmol) was added

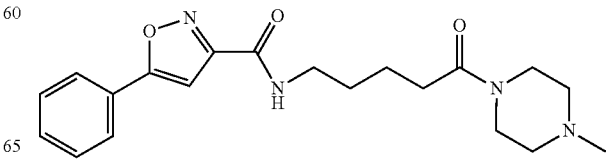

Example 43

N-(5-(4-methylpiperazin-1-yl)-5-oxopentyl)-5-phenylisoxazole-3-carboxamide: To a stirred solution of 5-phenylisoxazole-3-carboxylic acid (0.5 g, 2.64 mmol) in DMF (10 mL) was added HATU (1.5 g, 3.96 mmol) at 0° C. The reaction was stirred at 0° C. for 30 min. 5-amino-1-(4-methylpiperazin-1-yl)pentan-1-one (0.526 g, 2.64 mmol) was added at 0° C. and the reaction was stirred for 15 min. Next, DIPEA (3.2 mL, 18.4 mmol) was added at 0° C. and the reaction was stirred at 25° C. for 1 h. Water was added (100 mL) and the resulting solid was filtered and dried under vacuum to give N-(5-(4-methylpiperazin-1-yl)-5-oxopentyl)-5-phenylisoxazole-3-carboxamide (0.120 g, 371 [M+H]). 1H NMR: (400 MHz, DMSO): δ: 1.535-1.543 (d, J=3.2, 4H), 2.202 (s, 3H), 2.281 (s, 2H), 2.335 (s, 4H), 3.262-3.278 (d, J=6.4, 2H), 3.439 (s, 4H), 7.364 (s, 1H), 7.553-7.568 (d, J=6, 3H), 7.931-7.950 (t, 2H), 8.844-8.857 (d, J=5.2, 1H).

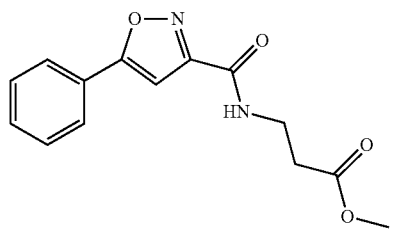 [SMILES: COC(=O)CCNC(=O)c1cc(-c2ccccc2)on1]

3-(5-phenylisoxazole-3-carboxamido)propanoate: To a stirred solution of 5-phenylisoxazole-3-carboxylic acid (5.0 g, 26.43 mmol) in DMF (50 mL) was added HATU (15.06 g, 39.63 mmol) at 0° C. The reaction mixture was stirred at 0° C. for 30 minutes and then methyl 3-aminopropanoate (3.65 g, 26.43 mmol) was added. After stirring 10 minutes, DIPEA (24 mL, 132.15 mmol) was added drop wise and the reaction stirred at 25° C. for 1 h. The reaction mixture was quenched in ice cold water and the resulting solid was filtered. The crude product was purified by column chromatography (10-15% ethyl acetate in hexane) to give methyl 3-(5-phenylisoxazole-3-carboxamido)propanoate (6.5 g, 275 [M+H]). 1H NMR: (400 MHz, DMSO): δ: 2.605-2.641 (t, 2H), 3.062 (s, 2H), 3.618 (s, 3H), 7.539-7.609 (m, 4H), 7.930-7.954 (dd, J=1.6, 7.2, 2H), 8.875-8.903 (t, 1H).

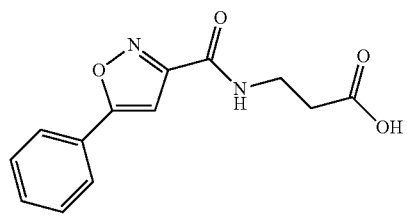 [SMILES: O=C(O)CCNC(=O)c1cc(-c2ccccc2)on1]

3-(5-phenylisoxazole-3-carboxamido)propanoic acid: To a stirred solution of methyl 3-(5-phenylisoxazole-3-carboxamido)propanoate (2.8 g, 10.2 mmol) in THF (20 mL) was added lithium hydroxide (1.67 g, 40.83 mmol) in water (20 mL) at 0° C. and the reaction was stirred at 25° C. for 2 h. The organic solvent was distilled off, water was added (20 mL), and acidified with aq. 5N HCl (20 mL). The solid precipitate was collected by filtration and dried under vacuum to give 3-(5-phenylisoxazole-3-carboxamido)propanoic acid (2.0 g, 261 [M+H]). 1H NMR: (400 MHz, DMSO): δ: 2.512-2.560 (dd, J=4.8, J=12, 2H), 3.456-3.506 (dd, J=7.2, J=12.8, 2H), 7.419 (s, 2H), 7.527-7.551 (m, 4H), 8.819-8.847 (t, 1H), 12.331 (s, 1H).

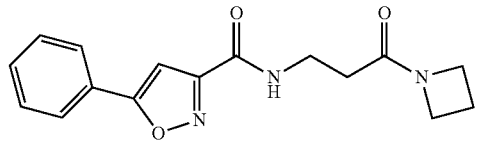 [SMILES: O=C(NCCC(=O)N1CCC1)c1cc(-c2ccccc2)on1]

Example 44

N-(3-(azetidin-1-yl)-3-oxopropyl)-5-phenylisoxazole-3-carboxamide: To a stirred solution of 3-(5-phenylisoxazole-3-carboxamido)propanoic acid (1.5 g, 5.763 mmol) in DMF (20 mL) was added HATU (3.28 g, 8.64 mmol) at 0° C. The reaction mixture was stirred at 0° C. for 30 minute and added azetidine HCl (0.539 g, 5.76 mmol) and After 10 minute DIPEA (2.99 mL, 17.29 mmol) was added drop wise and stirred at 25° C. for 1 h. Reaction mixture was quench in ice cold water and solid mass was filter out. The crude product was purified by column chromatography; pure product was eluted in 0-2% methanol in MDC to give N-(3-(azetidin-1-yl)-3-oxopropyl)-5-phenylisoxazole-3-carboxamide (0.792 g, 300 [M+H]). 1H NMR: (400 MHz, DMSO): δ 2.135-2.212 (dd, J=8, 15.6, 2H), 2.317-2.352 (t, 2H), 3.352-3.472 (dd, J=6, 6.8, 2H), 3.824-3.862 (t, 2H), 4.085-4.123 (t, 2H), 7.381 (s, 1H), 7.553-7.567 (d, J=5.6, 3H), 7.934-7.953 (t, 2H), 8.787 (s, 1H).

Representative compounds of the invention are prepared similarly from 5-(5-phenylisoxazole-3-carboxamido)propanoic acid and the corresponding amine.

| Example | | LC/MS m/z |
|---|---|---|
| 45. |  | 314 [M + H] |
| 46. |  | 358 [M + H] |
| 47. |  | 337 [M + H] |

| Example | | LC/MS m/z |
|---|---|---|
| 48. | 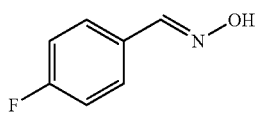 | 343 [M + H] |
| 49. | | 357 [M + H] |
| 50. | 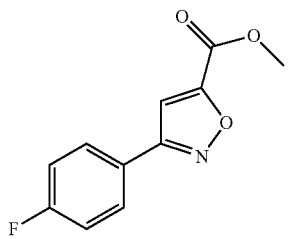 | 337 [M + H] |

(E)-4-fluorobenzaldehydeoxime: To a stirred solution of 4-fluorobenzaldehyde (10.0 g, 80.53 mmol) and sodium acetate (11.2 g, 136.84 mmol) in methanol (20 mL) was added hydroxylamine hydrochloride (6.0 g 88.49 mmole) and the reaction was stirred for 2 h at 25° C. The reaction mixture was diluted with water (150 mL) and the resulting solid precipitate was filtered and dried under vacuum to obtain (E)-4-fluorobenzaldehydeoxime (5.5 g). 1H NMR: (400 MHz, DMSO) (29542) δ: 7.221-7.266 (t, 2H), 7.630-7.665 (m, 2H), 8.154 (s, 1H), 11.256 (s, 1H).

Methyl 3-(4-fluorophenyl)isoxazole-5-carboxylate: To a stirred solution (E)-4-fluorobenzaldehydeoxime (5.5 g, 39.53 mmol) in water (20 mL) was added methyl propiolate (8.3 g, 98.82 mmol) and potassium chloride (2.9 g, 39.53 mmol) at 0° C. The mixture was stirred for 10 minutes. Oxone (36.45 g, 59.29 mmol) was added portion wise at 0° C. and the reaction was stirred at 25° C. for 2 h. The reaction mixture was diluted with water (30 mL) and extracted in dichloromethane (50 mL×2). The organic layer was washed with brine, dried over anhydrous sodium sulphate and concentrated to obtain crude product which was purified by column chromatography (0-50% ethyl acetate in hexane) to obtain methyl 3-(4-fluorophenyl)isoxazole-5-carboxylate (3.0 g). 1H NMR: 400 MHz, DMSO) (30008) δ: 3.809 (s, 3H), 7.616-7.648 (m, 2H), 7.784 (s, 1H), 7.793-7.784 (m, 2H).

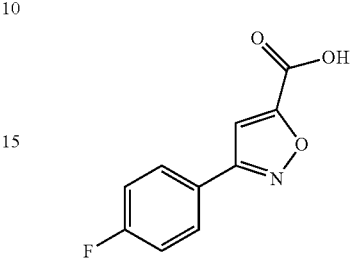

3-(4-fluorophenyl)isoxazole-5-carboxylic acid: To a stirred solution of methyl 3-(4-fluorophenyl)isoxazole-5-carboxylate (4.5 g, 19.80 mmol) in 1,4-dioxane (40 mL) was added 1N NaOH (21.0 mL) drop wise at 0° C. The reaction mixture was stirred for 2 h at 25° C. Dioxane was evaporated off and water (20 mL) was added and acidified using 1N HCl (25 mL). The resulting solid precipitate was filtered, washed with water and dried under vacuum to obtain 3-(4-fluorophenyl)isoxazole-5-carboxylic acid (2.5 g).

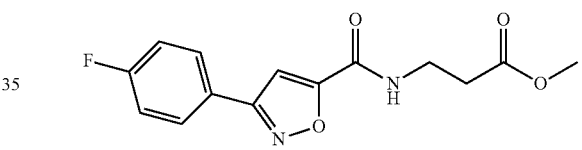

methyl 3-(3-(4-fluorophenyl)isoxazole-5-carboxamido)propanoate: To a stirred solution of 3-(4-fluorophenyl)isoxazole-5-carboxylic acid (1.0 g 4.82 mmol) and methyl 3-aminopropanoate (1.0 g, 7.24 mmol) in a 1:1 mixture of dichloromethane:ethyl acetate (20 mL) was added DIPEA (5.18 mL, 28.92 mmol) at 0° C. under nitrogen atmosphere and the solution was stirred for 30 minutes. Next, 1-propanephosphonic anhydride (50% Solution in ethyl acetate) (2.3 mL, 7.24 mmol) was added drop-wise and the reaction mixture was stirred at 25° C. for 2 h. The solvent was distilled off and the reaction mixture was diluted with water (15 mL) to form solid precipitate that was filtered. The solid was dried under vacuum to obtain methyl 3-(3-(4-fluorophenyl)isoxazole-5-carboxamido)propanoate. (0.7 g, 293 [M+H]). 1H NMR: (400 MHz, DMSO) δ: 2.613-2.648 (t, 2H), 3.491-3.540 (q, 2H), 3.619 (s, 3H), 7.366-7.410 (t, 2H), 7.660 (s, 1H), 7.978-8.014 (m, 2H), 9.011-9.136 (t, 1H).

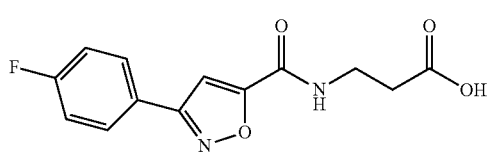 [SMILES: O=C(O)CCNC(=O)c1cc(-c2ccc(F)cc2)no1]

3-(3-(4-fluorophenyl)isoxazole-5-carboxamido)propanoic acid: To a stirred solution of methyl 3-(3-(4-fluorophenyl)isoxazole-5-carboxamido)propanoate (0.7 g, 2.391 mmol) in THF (10 mL) was added lithium hydroxide (0.401 g, 9.565 mmol) solution in water (5 mL) drop-wise at 0° C. The reaction mixture was stirred for 2 h at 25° C. THF was distilled off, water (10 mL) was added and the aqueous solution was acidified using 1N HCl (25 mL). The resulting solid precipitate was filtered, washed with water and dried under vacuum to obtain 3-(3-(4-fluorophenyl)isoxazole-5-carboxamido)propanoic acid (0.5 g, 277 [M+H]).

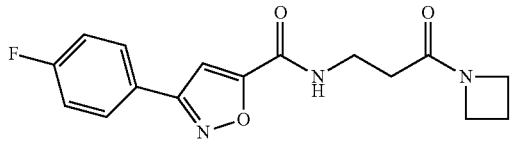 [SMILES: O=C(NCCC(=O)N1CCC1)c1cc(-c2ccc(F)cc2)no1]

Example 51

N-(3-(azetidin-1-yl)-3-oxopropyl)-3-(4-fluorophenyl) isoxazole-5-carboxamide: To a stirred solution of 3-(3-(4-fluorophenyl)isoxazole-5-carboxamido)propanoic acid (0.3 g, 1.083 mmol) and azetidine-HCl (0.151 g, 1.62 mmol) in a 1:1 solution of dichloromethane:ethyl acetate (10 mL) was added DIPEA (1.16 mL, 6.498 mmol) at 0° C. under nitrogen atmosphere. The solution was stirred for 30 minutes and then 1-propanephosphonic anhydride (50% Solution in ethyl acetate) (1.0 mL, 1.62 mmol) was added drop-wise to the reaction mixture. The resulting mixture was stirred at 25° C. for 2 h. Solvent was distilled off and the residue was diluted with water (15 mL). The resulting solid precipitate was filtered and washed with water to obtained crude product which was purified by Prep HPLC to give N-(3-(azetidin-1-yl)-3-oxopropyl)-3-(4-fluorophenyl)isoxazole-5-carboxamide (0.070 g, 318 [M+H]). $^1$H NMR: (400 MHz, DMSO) δ: 2.140-2.217 (m, 2H), 2.324-2.360 (t, 2H), 3.443-3.475 (t, 2H), 3.827-3.868 (t, 2H), 4.085-4.123 (t, 2H), 7.373-7.418 (t, 2H), 7.653 (s, 1H), 7.980-8.016 (m, 2H), 9.008-9.035 (t, 1H).

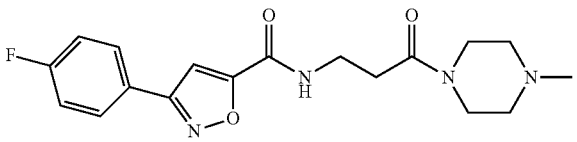 [SMILES: CN1CCN(C(=O)CCNC(=O)c2cc(-c3ccc(F)cc3)no2)CC1]

Example 52

3-(4-fluorophenyl)-N-(3-(4-methylpiperazin-1-yl)-3-oxopropyl)isoxazole-5-carboxamide: To a stirred solution of 3-(3-(4-fluorophenyl)isoxazole-5-carboxamido)propanoic acid (0.300 g, 1.083 mmol) and 1-methylpiperazine (0.162 g, 1.62 mmol) in 1:1 dichloromethane:ethyl acetate (10 mL) was added DIPEA (0.9 mL, 5.49 mmol) at 0° C. under nitrogen atmosphere and the mixture stirred for 30 minutes. 1-Propanephosphonic anhydride (50% Solution in ethyl acetate) (1.0 mL, 1.62 mmol) was added drop wise to the reaction mixture and the reaction was stirred at 25° C. for 2 h. Solvent was distilled off and reaction mixture was diluted with water (15 mL). The precipitate was filtered and dried under vacuum to obtain 3-(4-fluorophenyl)-N-(3-(4-methyl-piperazin-1-yl)-3-oxopropyl)isoxazole-5-carboxamide (0.060 g, 361 [M+H]). 1H NMR (400 MHz, DMSO) δ: 2.236 (s, 3H), 2.339-2.385 (m, 4H), 2.612-2.648 (t, 2H), 3.458-3.506 (q, 6H), 7.372-7.416 (t, 2H), 7.660 (s, 1H), 7.919-8.015 (m, 2H), 8.975-9.002 (t, 1H).

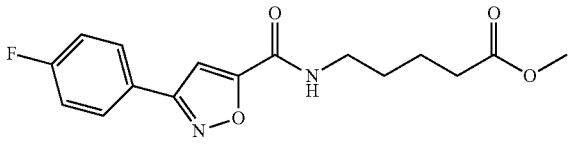 [SMILES: COC(=O)CCCCNC(=O)c1cc(-c2ccc(F)cc2)no1]

5-(3-(4-fluorophenyl)isoxazole-5-carboxamido)pentanoate: To a stirred solution of 3-(4-fluorophenyl)isoxazole-5-carboxylic acid (1.0 g, 4.82 mmol) and methyl 5-aminopentanoate (1.1 g, 7.24 mmol) in 1:1 dichloromethane:ethyl acetate (20 mL) was added DIPEA (5.18 mL, 28.92 mmol) at 0° C. under nitrogen atmosphere and the mixture was stirred for 30 minutes. 1-Propanephosphonic anhydride (50% Solution in ethyl acetate) (2.3 mL 7.24 mmol) was added drop wise at 0° C. and the reaction was stirred at 25° C. for 2 h. Solvent was distilled off and residue was diluted with water (15 mL). The solid precipitate was filtered and dried under vacuum to obtained methyl 5-(3-(4-fluorophenyl)isoxazole-5-carboxamido)pentanoate. (0.700 g, 321 [M+H]). 1H NMR: (400 MHz, DMSO) (30245) δ: 1.541-1.547 (d, 4H), 2.327-2.343 (d, J=6.4, 2H), 3.259-3.287 (t, 2H), 3.490.3.576 (t, 3H), 7.361-7.402 (t, 2H), 7.590-7.599 (d, J=3.6, 1H), 7.967-7.997 (t, 3H), 9.051-9.079 (t, 1H).

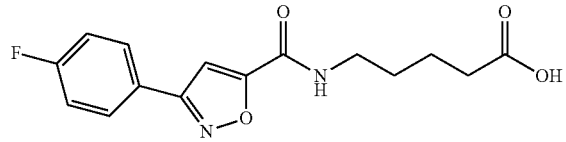 [SMILES: O=C(O)CCCCNC(=O)c1cc(-c2ccc(F)cc2)no1]

5-(3-(4-fluorophenyl)isoxazole-5-carboxamido)pentanoic acid: To a stirred solution of methyl 5-(3-(4-fluorophenyl) isoxazole-5-carboxamido)pentanoate of (0.7 g, 2.391 mmol) in THF (10 mL) was added lithium hydroxide (0.4 g, 9.565 mmol) solution in water (5 mL) drop wise at 0° C. The reaction mixture was stirred for 2 h at 25° C. THF was distilled off, water was added and acidified using 1N HCl (25 mL). The precipitate was filtered, washed with water, and dried under vacuum to obtain 5-(3-(4-fluorophenyl) isoxazole-5-carboxamido)pentanoic acid (0.5 g, 307 [M+H]). $^1$H NMR: (400 MHz, DMSO) δ: 1.539-1.546 (d, J=2.8, 4H), 2.239-2.272 (t, 2H), 3.265-3.279 (d, J=5.6, 2H), 7.367-7.411 (t, 2H), 7.632 (s, 1H). 7.977-7.999 (m, 2H), 9.031-9.051 (t, 1H).

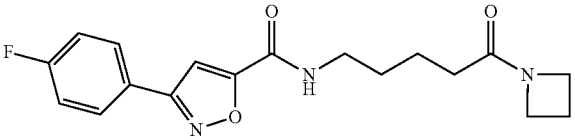 [SMILES: O=C(NCCCCC(=O)N1CCC1)c1cc(-c2ccc(F)cc2)no1]

Example 53

N-(5-(azetidin-1-yl)-5-oxopentyl)-3-(4-fluorophenyl) isoxazole-5-carboxamide: To a stirred solution of 5-(3-(4-fluorophenyl)isoxazole-5-carboxamido)pentanoic acid (0.17 g, 0.555 mmol) and azetidine-HCL (0.077 g, 0.833 mmol) in 1:1 dichloromethane:ethyl acetate (10 mL) was added DIPEA (1.16 mL, 6.498 mmol) at 0° C. under nitrogen atmosphere and the mixture stirred for 30 minutes. 1-Propanephosphonic anhydride (50% Solution in ethyl acetate) (0.53 mL, 0.833 mmol) was added drop wise to the reaction mixture and the reaction was stirred at 25° C. for 2 h. Solvent was distilled off and the residue was diluted with water (15 mL). The precipitate was filtered and dried under vacuum to obtain N-(5-(azetidin-1-yl)-5-oxopentyl)-3-(4-fluorophenyl)isoxazole-5-carboxamide (0.050 g, 346 [M+H]). $^1$H NMR: (400 MHz, DMSO) δ: 1.507-1.515 (d, J=3.2, 4H), 2.024-2.05 (t, 2H), 2.143-2.162 (t, 2H), 3.343 (s, 2H), 3.793-3.812 (t, 2H), 4.073-4.11 (t, 2H), 7.373-7.417 (t, 2H), 7.636 (s, 1H), 7.981-8.017 (m, 2H), 9.026-9.054 (t, 1H).

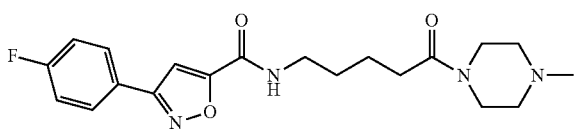 [SMILES: CN1CCN(C(=O)CCCCNC(=O)c2cc(-c3ccc(F)cc3)no2)CC1]

Example 54

3-(4-fluorophenyl)-N-(5-(4-methylpiperazin-1-yl)-5-oxopentyl)isoxazole-5-carboxamide): To a stirred solution of 5-(3-(4-fluorophenyl)isoxazole-5-carboxamido)pentanoic acid (0.17 g, 0.555 mmol) and 1-methylpiperazine (0.0797 g, 0.833 mmol) in 1:1 dichloromethane:ethyl acetate (10 mL) was added DIPEA (1.16 mL, 6.498 mmol) at 0° C. under nitrogen atmosphere and stirred for 30 minutes. 1-Propanephosphonic anhydride (50% Solution in ethyl acetate) (0.53 mL, 0.833 mmol) was added drop wise to the reaction mixture and the reaction was stirred at 25° C. for 2 h Solvent was distilled off and the residue was diluted with water (15 mL). The precipitate was filtered and dried under vacuum to obtain 3-(4-fluorophenyl)-N-(5-(4-methylpiperazin-1-yl)-5-oxopentyl)isoxazole-5-carboxamide (0.040 g 389 [M+H]). $^1$H NMR: (400 MHz, DMSO) δ: 1.536 (s, 4H), 2.158 (s, 3H), 2.216 (s, 2H), 2.269 (s, 2H), 2.330 (s, 2H), 3.282-3.266 (d, J=6.4, 2H), 3.420 (s, 4H), 7.414-7.312 (t, 2H), 7.414 (s. 1H), 8.013-7.980 (t, 2H), 9.059-9.045 (d, J=5.6, 1H).

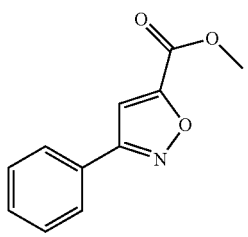

Methyl 3-phenylisoxazole-5-carboxylate: To a stirred solution (E)-benzaldehydeoxime (5.0 g, 41.21 mmol) in water (20 mL) was added methyl propiolate (8.6 g, 103.18 mmol) and potassium chloride (3.07 g, 41.21 mmol) at 0° C. and stirred for 10 minutes. Oxone (38.0 g, 61.81 mmol) was added portion wise at 0° C. and the reaction was stirred at 25° C. for 2 h. The reaction mixture was diluted with water (30 mL) and extracted in dichloromethane (50 mL×2). The organic layer was washed with brine, dried over anhydrous sodium sulphate and concentrated to obtain crude which was purified by column chromatography and the product was eluted at 0-50% ethyl acetate in hexane system to obtain methyl 3-phenylisoxazole-5-carboxylate (4.0 g, 203.20[M+H]). $^1$H NMR: (400 MHz, DMSO) (30737) δ: 3.937 (s, 3H), 7.503-7.547 (m, 3H), 7.929 (s, 1H), 7.943-7.985 (m, 2H).

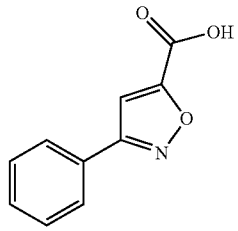 [SMILES: O=C(O)c1cc(-c2ccccc2)no1]

3-phenylisoxazole-5-carboxylate: To a stirred solution of methyl 3-phenylisoxazole-5-carboxylate (4.5 g, 19.80 mmol) in 1,4-dioxane (40 mL) was added 1N NaOH (21.12 mL) added drop wise at 0° C. The reaction mixture was stirred for 2 h at 25° C. Dioxane was distilled off and the crude mixture was diluted with water (20 mL) and acidified using 1N HCl (25 mL). The resulting precipitate was filtered, washed with water and dried under vacuum to obtain 3-phenylisoxazole-5-carboxylic acid (2.2 g).

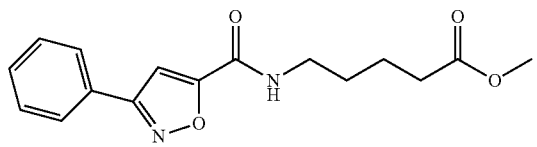 [SMILES: COC(=O)CCCCNC(=O)c1cc(-c2ccccc2)no1]

methyl 5-(3-phenylisoxazole-5-carboxamido)pentanoate: To a stirred solution of 3-phenylisoxazole-5-carboxylic acid (1.0 g, 5.28 mmol) and methyl 5-amino pentanoate (1.3 g, 7.929 mmol) in dichloromethane:ethyl acetate (10:10 mL) was added DIPEA (5.6 mL, 31.68 mmol) at 0° C. under nitrogen atmosphere and stirred for 30 minutes. Then, 1-propanephosphonic anhydride (50% Solution in ethyl acetate) (2.5 mL 7.929 mmol) was added drop-wise at 0° C. and the reaction mixture was stirred at 25° C. for 2 h. The solvent was distilled off and the reaction mixture was to diluted with water (15 mL). The resulting was collected by filtration and dried under vacuum to obtain methyl 5-(3-phenylisoxazole-5-carboxamido)pentanoate (0.800 g, 302.95[M+H]). $^1$H NMR: (400 MHz, DMSO) (31021) δ: 1.237 (s, 2H), 1.551-1.587 (q, 4H), 2.340-2.375 (t, 2H), 3.252-3.298 (q, 2H), 3.589 (s, 3H), 7.538-7.555 (t, 3H), 7.632 (s, 1H), 7.920-7.944 (m, 2H), 9.068-9.040 (t, 1H).

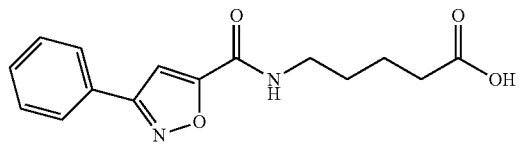 [SMILES: O=C(O)CCCCNC(=O)c1cc(-c2ccccc2)no1]

5-(3-phenylisoxazole-5-carboxamido)pentanoic acid: To a stirred solution methyl 5-(3-phenylisoxazole-5-carboxamido)pentanoate of (0.8 g, 2.64 mmol) in tetrahydrofuran (10 mL) was added lithium hydroxide (0.44 g, 10.54 mmol) solution in water (5 mL) drop wise at 0° C. The reaction mixture was stirred for 2 h at 25° C. and tetrahydrofuran was distilled off. The remaining aqueous was acidified using 1N HCl (25 mL) and the resulting precipitate was filtered and washed with water. The precipitate was dried under vacuum to obtain 5-(3-phenylisoxazole-5-carboxamido)pentanoic acid (0.630 g, 288.89[M+H]).

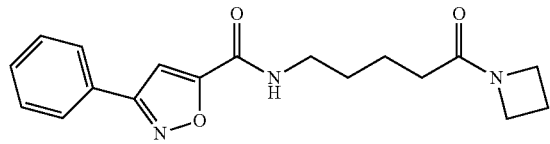 [SMILES: O=C(NCCCCC(=O)N1CCC1)c1cc(-c2ccccc2)no1]

Example 55

N-(5-(azetidin-1-yl)-5-oxopentyl)-3-phenylisoxazole-5-carboxamide: To a stirred solution of 5-(3-phenylisoxazole-5-carboxamido)pentanoic acid (0.2 g, 0.694 mmol) and azetidine-HCl (0.97 g, 0.833 mmol) in dichloromethane:ethyl acetate (1:1, 10.0 mL) was added DIPEA (0.74 mL, 4.164 mmol) and at 0° C. under nitrogen atmosphere and stirred for 30 minutes. 1-propanephosphonic anhydride (T3P) (50% Solution in ethyl acetate) (0.66 mL, 1.041 mmol) was added drop wise in the reaction mixture and stirred at 25° C. for 2 h. The organic solvent was distilled off and the crude reaction mixture was diluted with water (15 mL). The resulting solid precipitate was filtered and dried under vacuum to obtain N-(5-(azetidin-1-yl)-5-oxopentyl)-3-phenylisoxazole-5-carboxamide (0.050 g, 327.38M+H]).
$^1$H NMR: (400 MHz, DMSO) (31492) δ: 1.511-1.527 (t, 4H), 2.026-2.059 (t, 2H), 2.124-2.200 (m, 2H), 3.244-3.274 (t, 2H), 3.794-3.833 (t, 2H), 4.074-4.112 (t, 2H), 7.539-7.555 (t, 3H) 7.626 (s, 1H), 7.920-7.944 (q, 2H), 9.019-9.046 (t, 1H).

Representative compounds of the invention are prepared similarly 3-(3-phenylisoxazole-5-carboxamido)pentanoic acid and the corresponding amine.

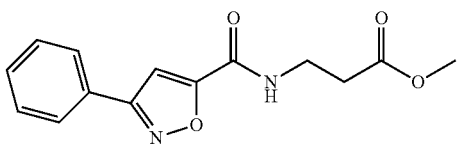 [SMILES: COC(=O)CCNC(=O)c1cc(-c2ccccc2)no1]

Methyl 3-(3-phenylisoxazole-5-carboxamido)propanoate: To a stirred solution of 3-phenylisoxazole-5-carboxylic acid (1 g, 4.82 mmol) and methyl 3-aminopropanoate (1.1 g, 7.29 mmol) in dichloromethane:ethyl acetate (5:5 mL) was added DIPEA (5.1 mL, 28.92 mmol) at 0° C. under nitrogen atmosphere. The reaction mixture was stirred for 30 minutes. After 10 min, 1-propanephosphonic anhydride (50% Solution in ethyl acetate) (2.3 mL, 7.24 mmol) was added drop wise and the reaction mixture was stirred at 25° C. for 2 h. The organic solvents were distilled off and the reaction crude mixture was diluted with water (15 mL). The resulting solid precipitate was filtered and dried under vacuum to obtain methyl 3-(3-phenylisoxazole-5-carboxamido)propanoate (0.800 g, 274.93[M+H]). 1H NMR: (400 MHz, DMSO) (31313) δ: 1.257-1.268 (d, J=4.4, 2H), 2.617-2.652 (t, 2H), 3.495-3.583 (q, 2H), 3.622 (s, 3H), 7.537-7.655 (t, 3H), 7.655 (s, 1H), 7.920-7.943 (m, 2H), 9.112-9.138 (t, 1H).

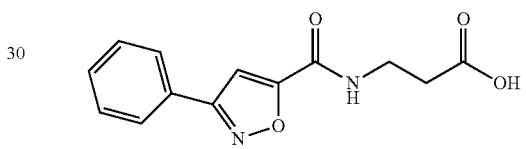

3-(3-phenylisoxazole-5-carboxamido)propanoic acid: To a stirred solution methyl 3-(3-phenylisoxazole-5-carbox-

| Example | | LC/MS m/z |
|---|---|---|
| 56. | ![structure] | 356 [M + H] |
| 57. | ![structure] | 344 [M + H] |
| 58. | ![structure] | 342 [M + H] |
| 59. | ![structure] | 371 [M + H] | amido)propanoate of (0.800 g, 2.94 mmol) in tetrahydrofuran (10 mL) was added lithium hydroxide (0.491 g, 11.72 mmol) solution in water (5 mL) drop wise at 0° C. The reaction mixture was stirred for 2 h at 25° C. and the tetrahydrofuran was distilled off. The remaining aqueous solution was acidified using 1N HCl (25 mL) and the resulting precipitate was filtered, washed with water and dried under vacuum to obtain 3-(3-phenylisoxazole-5-carboxamido)propanoic acid (0.430 g, 258.9[M+H])

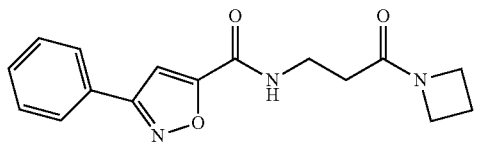 [SMILES: O=C(NCCC(=O)N1CCC1)c1cc(-c2ccccc2)no1]

Example 60

N-(3-(azetidin-1-yl)-3-oxopropyl)-3-phenylisoxazole-5-carboxamide: To a stirred solution of 3-(3-phenylisoxazole-5-carboxamido)propanoic acid (0.200 g, 0.764 mmol) and azetidine-HCl (0.8.2 mL, 4.615 mmol) in dichloromethane: ethyl acetate (1:1, 10.0 mL) was added DIPEA (0.74 mL, 4.164 mmol) at 0° C. under nitrogen atmosphere. The reaction mixture was stirred for 30 minutes. Next, 1-propanephosphonic anhydride (T3P) (50% Solution in ethyl acetate) (0.73 mL, 1.15) was added drop wise to the reaction mixture which was then stirred at 25° C. for 2 h. The organic solvents were distilled off and the reaction crude mixture was diluted with water (15 mL). The resulting solid precipitate was filtered and dried under vacuum to obtain crude product which was purified by Prep HPLC to give N-(3-(azetidin-1-yl)-3-oxopropyl)-3-phenylisoxazole-5-carboxamide (0.050 g, 300.04M+H]). $^1$H NMR: (400 MHz, DMSO) (32172) δ: 2.141-2.216 (m, 2H), 2.328-2.364 (t, 2H), 3.430-3.480 (q, 2H), 3.828-3.867 (t, 2H), 4.086-4.124 (t, 2H), 7.539-7.555 (t, 3H), 7.644 (s, 2H), 7.919 (m, 2H), 9.005-9.032 (t, 1H).

Representative compounds of the invention are prepared similarly 3-(3-phenylisoxazole-5-carboxamido)propanoic acid and the corresponding amine.

| Example | | LC/MS m/z |
|---|---|---|
| 61. | | 316 [M + H] |
| 62. | | 328 [M + H] |
| 63. | | 343 [M + H] |
| 64. | | 314 [M + H] |

Assays for Detecting and Measuring the Effect of Compounds on dF508-CFTR Channels CFRT-YFP High Throughput Assay:

The following protocol is designed to selectively screen small molecule compounds for F508del CFTR corrector activities in the HTS YFP flux assay. In this protocol, the cells are incubated with test compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human ΔF508-CFTR and a halide-sensitive yellow fluorescent protein (YFP-H148Q/I152L 25, 22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/mL, and streptomycin 100 µg/mL. G418 (0.75-1.0 mg/mL) and zeocin (3.2 µg/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Test compounds were applied to the cells at varying concentrations. Cells were incubated in a cell culture incubator at 37° C. with 5% $CO_2$ for 24-26 h. Assay plates were washed with DPBS media (Thermo, cat#SH30028.02) to remove unbound cells and compound. Stimulation media (25 µL) containing 20 µM Forskolin & 30 µM P3 [6-(Ethylphenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al., (2010).

REFERENCES

Galietta, L. J., Jayaraman, S., and Verkman, A. S. Cell-based assay for high-throughput quantitative screening of CFTR chloride transport agonists. Am. J. Physiol Cell Physiol 281(5), C1734, 2001.

Sui J, Cotard S, Andersen J, Zhu P, Staunton J, Lee M, Lin S. (2010) Optimization of a Yellow fluorescent protein-based iodide influx high-throughput screening assay for cystic fibrosis transmembrane conductance regulator (CFTR) modulators. Assay Drug Dev Technol. 2010 December; 8(6):656-68.

Determination of Activity in Primary CF Cell:

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay test compounds were added to the basolateral surface of the cells at various test concentrations dissolved in DMSO. Duplicate wells were prepared giving a n=3 or n=4 protocol.

6.1.2 Electrophysiological Procedures

Cells were treated for 24 hours with various combinations and concentrations of the test articles, reference standard (3 µM VX809, positive control). Compounds stock solutions were prepared in DMSO and diluted ⅟1000 into ALI media to their final assay concentration. Cells were treated with combination solutions (2 mL of each dilution) and incubated at 37° C. for 24 h.

Ussing:

For an Ussing experiment, cells on four Snapwell (6-well) plates were treated 24 hours prior to experimentation. The next day filters from individual Snapwells were removed from the plates and mounted vertically in Ussing chambers pre-equilibrated at 37° C. in 5 ml of HBS (pH 7.4) both apical and basolateral sides and bubbled with room air to facilitate mixing upon addition of compounds. The resting current was recorded for 10 min to ensure a stable baseline. Resting current was blocked by the apical addition of 3 µM benzamil, an ENaC inhibitor. After 10 min, 1 µM forskolin was added to both the apical and basolateral side to stimulate CFTR. The increase in chloride current was detected as an upward deflection of the trace. After an additional 10 min, the potentiator VX770 (1 µM) was added, further increasing the chloride current. Finally CFTR-172 (a CFTR inhibitor, 2 µM) and/or bumetanide (20 µM) was added to block CFTR mediated chloride current, resulting in a decrease in the observed current.

For the equivalent current assay, cells on four Transwell (24-well) plates were treated. Each Transwell plate was filled with 200 µl of HBS on the apical surface and 2 ml on the basolateral surface. Plates were placed horizontally in a heated mount at 37° C., and equilibrated for several minutes. Resting current was measured for 15 min and then blocked by the apical addition of 5 µM benzamil. After 20 min, 10 µM forskolin and 1 µM VX770 were added to both the apical and basolateral side to stimulate CFTR. An increase in chloride current is seen as an upward deflection of the trace. After another 30 min, CFTR-172 (a CFTR inhibitor, 2 µM) and/or bumetanide (20 µM) was added to block CFTR mediated chloride current.

Data Collection and Analysis Methods

The raw data, current vs. time for the Ussing chamber (sampling interval: 10 s) and voltage vs. time and resistance vs. time for the equivalent current assay (sampling interval: 5 minutes) were transferred to Excel (Microsoft Office Professional, version 14.0.7106.5003) for analysis. CFTR specific current was measured as the average amplitude of the increase in current elicited upon addition forskolin and ending upon addition of the CFTR channel specific blocker CFTR-172. This average is equivalent to the sum of the average forskolin activated and the average VX770-potentiated currents. The average current measured in vehicle (0.1% DMSO) treated cells, Iv, was subtracted from the current for the test article, $I_{TA}$, or from the corrector reference standard VX809 (3 µM $I_{STD}$. For replicate measurements, the average vehicle subtracted response for the test article, was normalized to the average vehicle subtracted inhibitor response of the reference corrector VX809 (3 µM).

$$I_{NSC}=(I_{TA}-I_V)_{(ave)}/(I_{STD}-I_V)_{(ave)} \quad \text{(Equation 1)}$$

A second endpoint, for the equivalent current assay, evaluated was NAUC, the normalized area under the curve (AUC) measuring the response after addition of forskolin and VX770 to the time point right before the addition of the CFTR inhibitor. The AUC is effectively the average response multiplied by the duration of the response. The AUC of the test article, $AUC_{TA}$ was then corrected by subtracting the average vehicle response, $AUC_{V,ave}$ over the same time range, and normalized as for the inhibitor-sensitive current to the difference of the corrector reference standard VX809 (3 µM $_{VX809r,ave}$ and the vehicle response:

$$NAUC_{TA}=[AUC_{TA}-AUC_{V,ave}]/[AUC_{VX809r,ave}-AUC_{V,ave}] \text{(Equation 2)}.$$

The normalized value for DMSO is 0.0 and for VX-809 alone is 1.0. Combinations of compounds with VX-809 that give normalized values greater than 1.0 show activity in the combination assay. A value of 2 means the test compound doubles the effect to VX-809 alone.

Experiments were run with a minimum of n=4 replicates per concentration. Since the distribution for the ratio of two normal distributions is a Cauchy distribution, the median value must be used for the average and the average deviation must be used for the error of all normalized data. Potency ($EC_{50}$) and efficacy (maximum response) were determined by fitting dose response data to a sigmoid dose response model (GraphPad Prism 5.04, Manufacturer) using Equation 3:

$$E=E_{min}+(E_{max}-E_{min})/(1+10^{((Log\ EC50-S)*n_H)}) \quad \text{(Equation 3)}$$

where E is the recorded response, and S is the concentration of test compound in combination with VX-809. Since there were at most 8 points in the dose response curve only $EC_{50}$ and maximum ($E_{max}$) were allowed to vary, while the minimum ($E_{min}$) was fixed equal to the VX-809 response of 1.0, and the Hill slope, $n_H$, was fixed equal to 1.

Statistical comparisons (t-test and Mann Whitney) and calculation of averages and errors were performed in Excel.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or

TABLE I

Equivalent current assay results in Primary CF airway epithelial cells;
The following meanings apply:
NAUC "+++" refers to an observed NAUC >170% of positive control
NAUC "++" refers to an observed NAUC 170-140% of positive control
NAUC "+" refers to an observed NAUC <140% of positive control

| Example No | Test Conc 3 uM | Test Conc 10 uM |
|---|---|---|
| 1 | ++ | +++ |
| 2 | ++ | +++ |
| 3 | ++ | +++ |
| 4 | ++ | +++ |
| 6 | ++ | +++ |
| 8 | +++ | +++ |
| 10 | ++ | +++ |
| 13 | + | ++ |
| 14 | +++ | +++ |
| 15 | +++ | +++ |
| 16 | +++ | +++ |
| 17 | + | ++ |
| 18 | ++ | ++ |
| 19 | + | + |
| 20 | + | ++ |
| 21 | + | ++ |
| 22 | + | ++ |
| 24 | ++ | ++ |
| 25 | + | + |
| 26 | +++ | +++ |
| 27 | ++ | ++ |
| 28 | + | + |
| 29 | ++ | ++ |
| 30 | ++ | ++ |
| 31 | ++ | ++ |
| 32 | + | + |
| 33 | + | + |
| 34 | + | + |
| 35 | ++ | +++ |
| 36 | ++ | +++ |
| 37 | + | ++ |
| 38 | +++ | +++ |
| 43 | +++ | +++ |
| 44 | +++ | +++ |
| 48 | +++ | +++ |
| 51 | ++ | +++ |
| 52 | ++ | +++ |
| 53 | ++ | +++ |
| 54 | ++ | +++ |
| 55 | ++ | +++ |
| 59 | +++ | +++ |
| 60 | +++ | +++ |
| 63 | +++ | +++ |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed:

1. A method of treating a disease or disorder selected from cystic fibrosis, asthma, constipation, hereditary emphysema, hereditary hemochromatosis, coagulation-fibrinolysis deficiencies, type 1 hereditary angioedema, familial hypercholesterolemia, type 1 chylomicronemia, abetalipoproteinemia, I-cell disease/pseudo-hurler, mucopolysaccharidoses, Sandhof/Tay-Sachs, Crigler-Najjar type II, polyendocrinopathy/hyperinsulinemia, diabetes mellitus, Laron dwarfism, myeloperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, Perlizaeus-Merzbacher disease, Alzheimer's disease, Parkinson's disease, amyotrophic lateral sclerosis, progressive supranuclear palsy, Pick's disease, Huntington's disease, Spinocerebullar ataxia type I, Spinal and bulbar muscular atrophy, Dentororubal pallidoluysian, Myotic dystrophy, Hereditary Creutzfeldt-Jakob disease, Fabry disease, Straussler-Scheinker disease, secretory diarrhea, polycystic kidney disease, chronic obstructive pulmonary disease, dry eye disease, Sjogren's Syndrome, spongiform encephalopathies and myotonic dystrophy, in a subject in need thereof, comprising the step of administering to the subject a therapeutically effective amount of a compound of Formula II

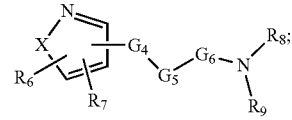

Formula II or a pharmaceutically acceptable salt thereof, wherein:

X is S or O;

$G_4$ is absent or is selected from —C(O)N($R_{10}$)—, —C(S)N($R_{10}$)—, —N($R_{10}$)—, —C(O)O—, —C(O)—, —C(S)—, —N($R_{11}$)C(O)N($R_{10}$)—, —S—, —O—, —SO—, —S(O)$_2$—, —S(O)$_2$N($R_{10}$)—, —C(S)O— and —C(S)N($R_{10}$);

each $R_{10}$ and $R_{11}$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

each $G_5$ is absent or is selected from a bivalent aliphatic, substituted aliphatic, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl;

$G_6$ is absent or is selected from —N($R_{10}$)C(O)—, —N($R_{10}$)C(S)—, —OC(O)—, —C(O)—, —C(S)—, —SO—, —S(O)$_2$—, —N($R_{10}$)S(O)$_2$—, —OC(S)— and —N($R_{10}$)C(S)—;

each $R_6$ and $R_7$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; alternatively $R_6$ and $R_7$ together with the atoms to which they are attached form an optionally substituted 3, 4, 5, 6 or 7 membered ring and, each $R_8$ and $R_9$ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; alternatively $R_8$ and $R_9$ groups together with the nitrogen atom to which they are attached form an optionally substituted 3, 4, 5, 6 or 7 membered ring.

2. The method of claim 1, wherein the compound of Formula II is represented by Formula I:

Formula I or a pharmaceutically acceptable salt, ester or prodrug thereof, wherein:

X is S or O;

G₁ is absent or selected from —C(O)N(R₁₀)—, —C(S)N(R₁₀)—, —N(R₁₀)—, —C(O)O—, —C(O)—, —C(S)—, —N(R₁₁)C(O)N(R₁₀)—, —S—, —O—, —SO—, —S(O)₂—, —S(O)₂N(R₁₀)—, —C(S)O— and —C(S)N(R₁₀);

each R₁₀ and R₁₁ is independently selected from hydrogen, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl;

each G₂ is absent or is selected from a bivalent aliphatic, substituted aliphatic, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl;

G₃ is absent or is selected from —N(R₁₀)C(O)—, —N(R₁₀)C(S)—, —OC(O)—, —C(O)—, —C(S)—, —N(R₁₁)C(O)—, —SO—, —S(O)₂—, —N(R₁₀)S(O)₂—, —OC(S)— and —N(R₁₀)C(S)—;

R₁ is selected from aryl, substituted aryl, heterocyclyl, substituted heterocyclyl, heteroaryl, and substituted heteroaryl;

each R₂ and R₃ is independently selected from hydrogen, halogen, —OR₁₀, —SR₁₀, —NR₁₀R₁₁, —CF₃, —CN, —NO₂, —N₃, —C(O)OR₁₀, —C(O)R₁₀, —C(O)NR₁₀R₁₁, —S(O)R₁₀, —S(O)NR₁₀, —S(O)₂R₁₀, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; and, n is 0, 1, 2, 3, 4, 5 or 6.

3. The method of claim 2 wherein the compound of Formula I is represented by Formula IA:

Formula IA or a pharmaceutically acceptably salt thereof, wherein:

s is 1, 2, 3 or 4;

each R₄ is independently hydrogen, halogen, —OR₂₀, —SR₂₀, —NR₂₀R₂₁, —C(O)R₂₀, —C(O)OR₂₀, —C(O)NR₂₀R₂₁, —N(R₂₀)C(O)R₂₁, —CF₃, —CN, —NO₂, —N₃, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; alternatively two R₄ together with the atoms to which they are attached form an optionally substituted 3, 4, 5, 6 or 7 membered ring; and, each R₂₀ and R₂₁ is selected from hydrogen, halogen, aliphatic, substituted aliphatic, aryl or substituted aryl.

4. The method of claim 2 wherein the compound of Formula II is represented by Formula IB or ID:

Formula IB

Formula ID or a pharmaceutically acceptable salt thereof;

wherein t is 1, 2, 3, 4, 5, 6, 7, 8, 9, 10, 11, 12, 13, 14, 15, 16 or 17.

5. The method according to claim 2, wherein G₁ is absent or selected from —C(O)N(R₁₀)—, —C(S)N(R₁₀)—, —N(R₁₀)—, —C(O)O—, —C(O)—, —C(S)—, —N(R₁₁)C(O)N(R₁₀)—, —S—, —O—, —SO—, —S(O)₂—, —S(O)₂N(R₁₀)—, —C(S)O— and —C(S)N(R₁₀).

6. The method according to claim 2, wherein G₁ is —C(O)NH.

7. The method according to claim 2, wherein G₂ is selected from:

-continued

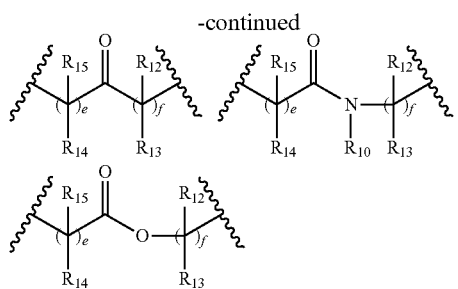

wherein:

e and f are independently selected from 0, 1, 2, 3, 4, 5, 6, 7, 8, 9 and 10;

d is 1, 2, 3, 4, 5, 6 or 7;

each $R_{12}$, $R_{13}$, $R_{14}$, and $R_{15}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; alternatively two $R_{10}$, $R_{11}$, $R_{12}$, $R_{13}$, $R_{14}$, and $R_{15}$ together with the atoms to which they are attached form an optionally substituted 3, 4, 5, 6 or 7 membered ring; and, each $R_{20}$ and $R_{21}$ is selected from hydrogen, halogen, aliphatic, substituted aliphatic, aryl or substituted aryl.

8. The method according to claim 2, wherein $R_1$ is selected from the Table below:

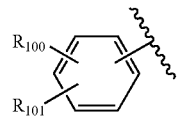

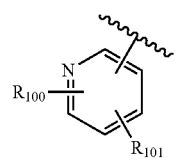

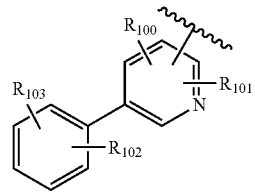

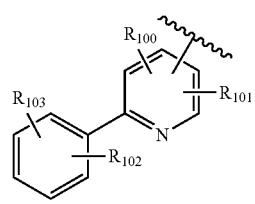

-continued

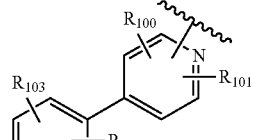

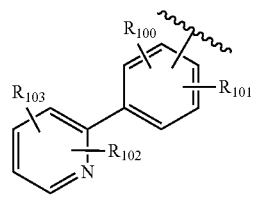

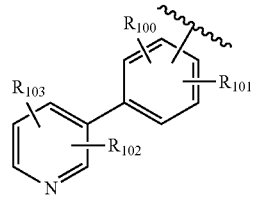

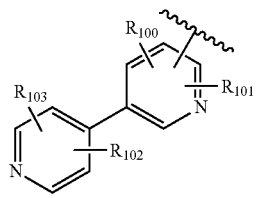

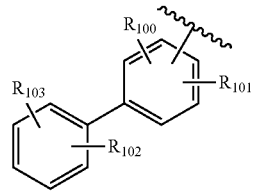

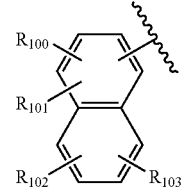

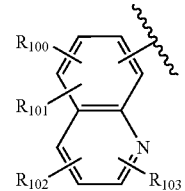

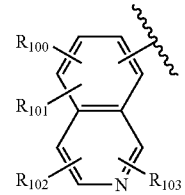

-continued

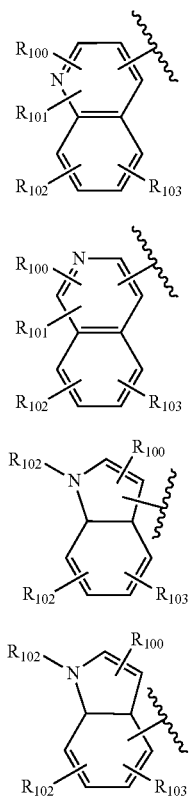

wherein each $R_{100}$, $R_{101}$, $R_{102}$ and $R_{103}$ is independently hydrogen, halogen, —$OR_{10}$, —$SR_{10}$, —$NR_{10}R_{11}$, —$C(O)R_{10}$, —$C(O)OR_{10}$, —$C(O)NR_{10}R_{11}$, —$N(R_{10})C(O)R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl and substituted aryl.

9. The method according to claim 2, wherein $R_1$ is selected from:

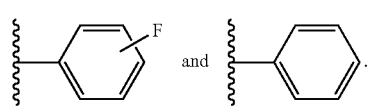

10. The method of claim 1, wherein the compound of Formula I is selected from Table A or a pharmaceutically acceptable salt thereof:

TABLE A

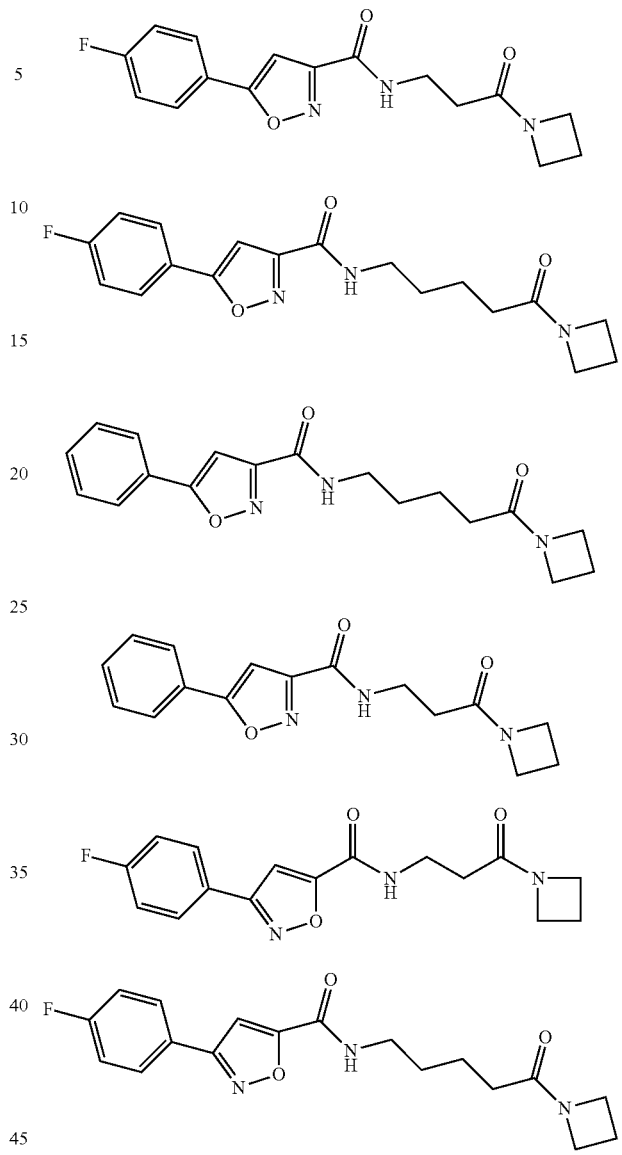

11. The method according to claim 1, wherein said compound of Formula II is administered in combination with a compound selected from Gentamicin, Genestein, Ataluren, Ivacaftor (Kalydeco), VX-661 and VX-809 or a combination thereof.

12. The method according to claim 1, wherein said compound of Formula II is selected from the table below or a pharmaceutically acceptable salt thereof:

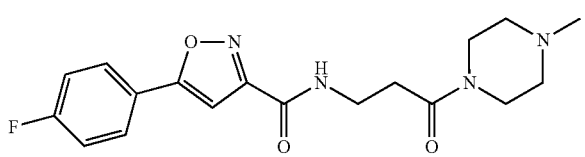 [SMILES: CN1CCN(C(=O)CCNC(=O)c2cc(-c3ccc(F)cc3)on2)CC1]

-continued
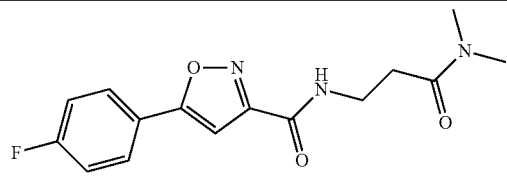
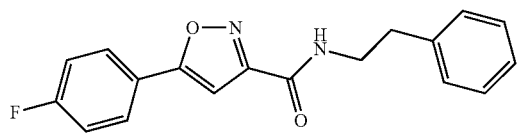 [SMILES: O=C(NCCc1ccccc1)c1cc(-c2ccc(F)cc2)on1]
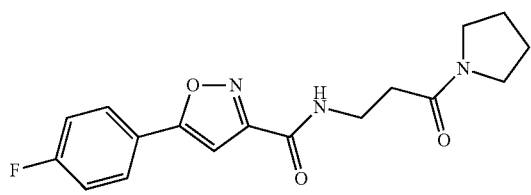 [SMILES: O=C(NCCC(=O)N1CCCC1)c1cc(-c2ccc(F)cc2)on1]
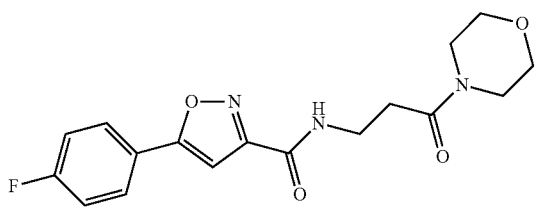 [SMILES: O=C(NCCC(=O)N1CCOCC1)c1cc(-c2ccc(F)cc2)on1]
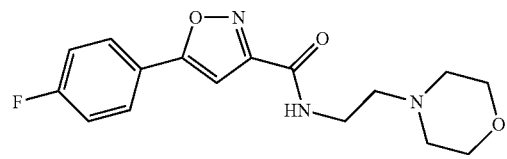 [SMILES: O=C(NCCN1CCOCC1)c1cc(-c2ccc(F)cc2)on1]
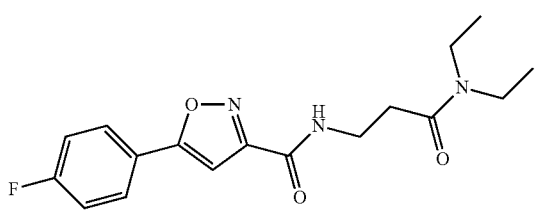 [SMILES: CCN(CC)C(=O)CCNC(=O)c1cc(-c2ccc(F)cc2)on1]
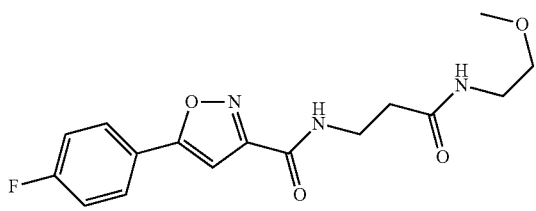 [SMILES: COCCNC(=O)CCNC(=O)c1cc(-c2ccc(F)cc2)on1]
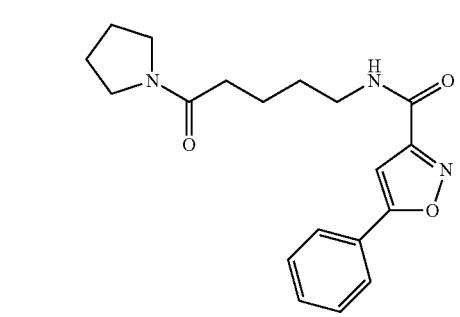 [SMILES: O=C(NCCCCC(=O)N1CCCC1)c1cc(-c2ccccc2)on1]

-continued
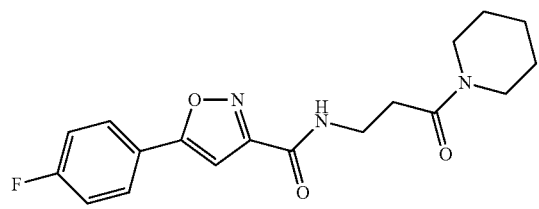
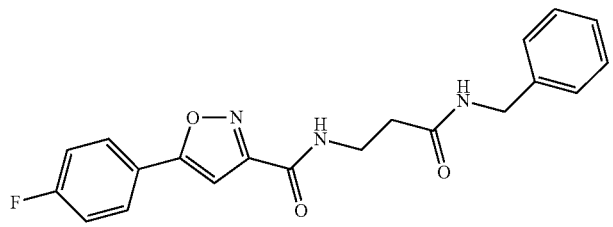 [SMILES: O=C(CCNC(=O)c1cc(-c2ccc(F)cc2)on1)NCc1ccccc1]
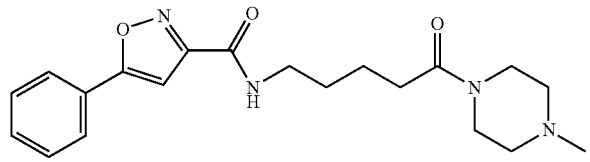 [SMILES: CN1CCN(C(=O)CCCCNC(=O)c2cc(-c3ccccc3)on2)CC1]
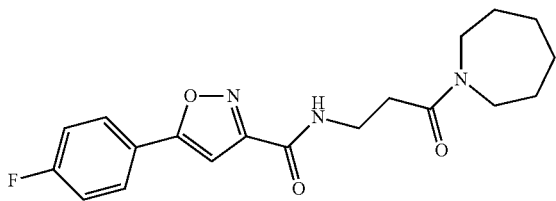 [SMILES: O=C(NCCC(=O)N1CCCCCC1)c1cc(-c2ccc(F)cc2)on1]
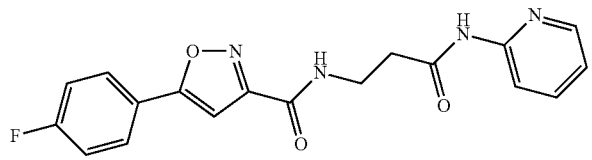 [SMILES: O=C(CCNC(=O)c1cc(-c2ccc(F)cc2)on1)Nc1ccccn1]
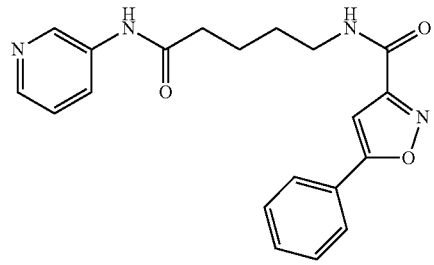 [SMILES: O=C(CCCCNC(=O)c1cc(-c2ccccc2)on1)Nc1cccnc1]
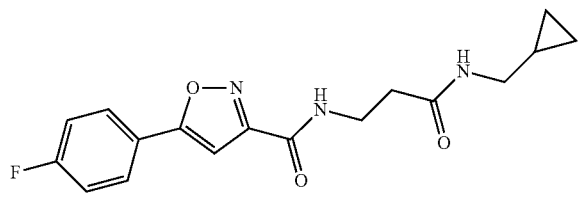 [SMILES: O=C(CCNC(=O)c1cc(-c2ccc(F)cc2)on1)NCC1CC1]

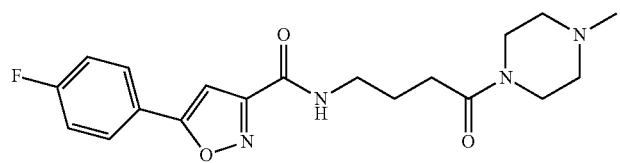 [SMILES: CN1CCN(C(=O)CCCNC(=O)c2cc(-c3ccc(F)cc3)on2)CC1]
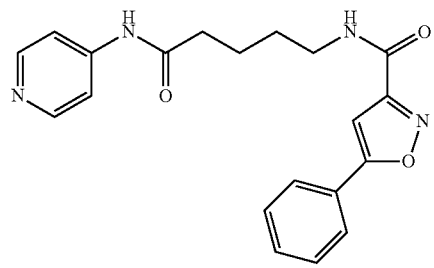 [SMILES: O=C(CCCCNC(=O)c1cc(-c2ccccc2)on1)Nc1ccncc1]
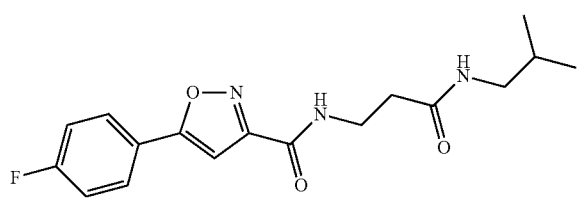 [SMILES: CC(C)CNC(=O)CCNC(=O)c1cc(-c2ccc(F)cc2)on1]
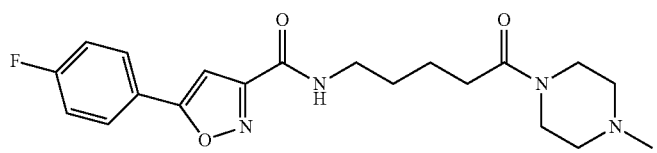 [SMILES: CN1CCN(C(=O)CCCCNC(=O)c2cc(-c3ccc(F)cc3)on2)CC1]
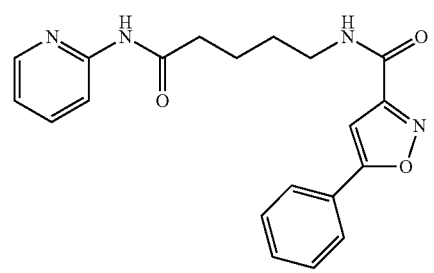 [SMILES: O=C(CCCCNC(=O)c1cc(-c2ccccc2)on1)Nc1ccccn1]
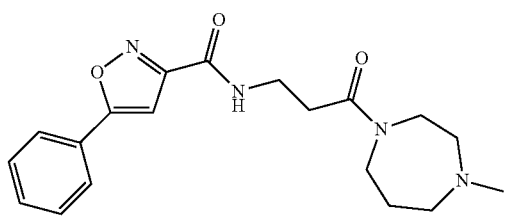 [SMILES: CN1CCCN(C(=O)CCNC(=O)c2cc(-c3ccccc3)on2)CC1]
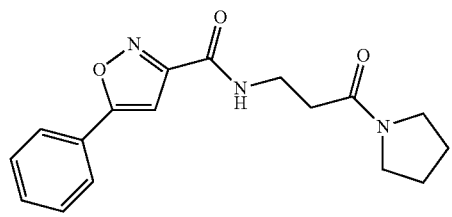 [SMILES: O=C(NCCC(=O)N1CCCC1)c1cc(-c2ccccc2)on1]

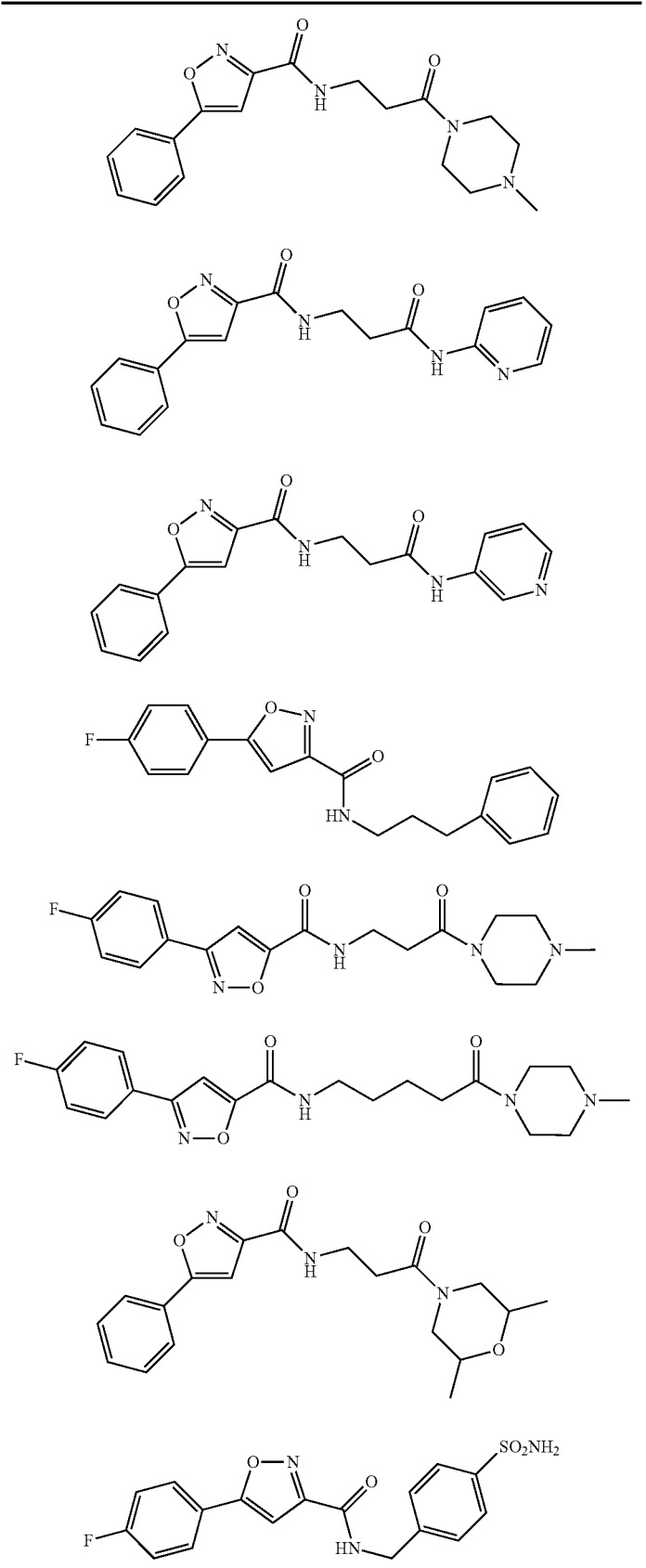

-continued
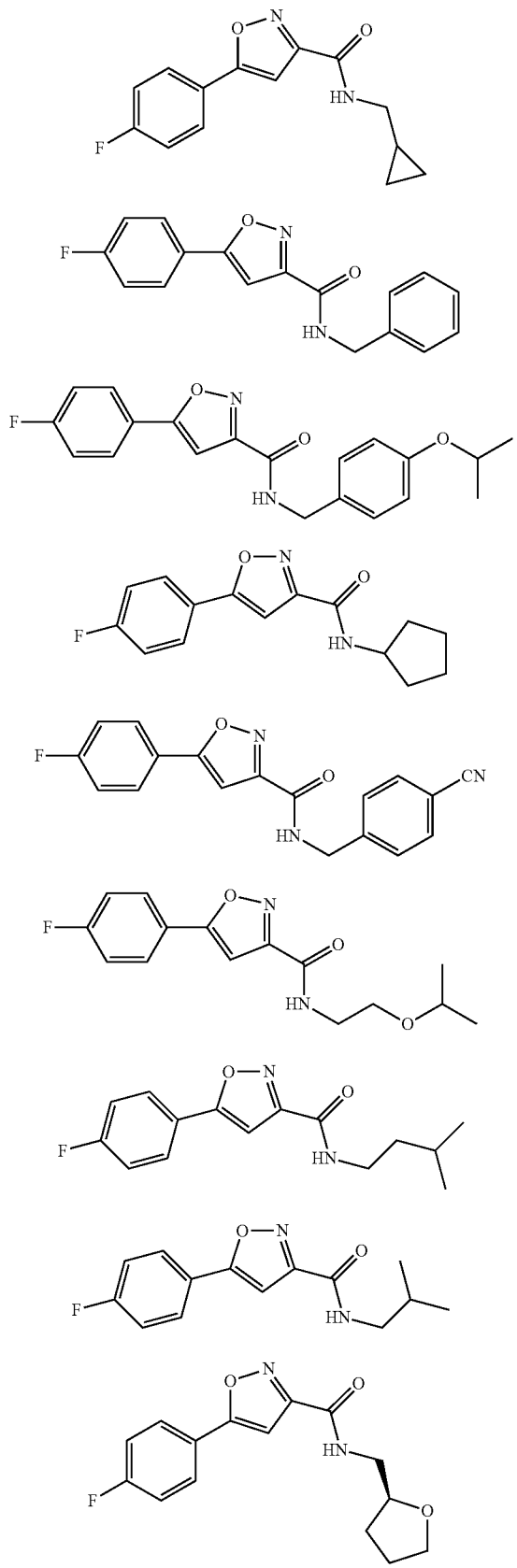

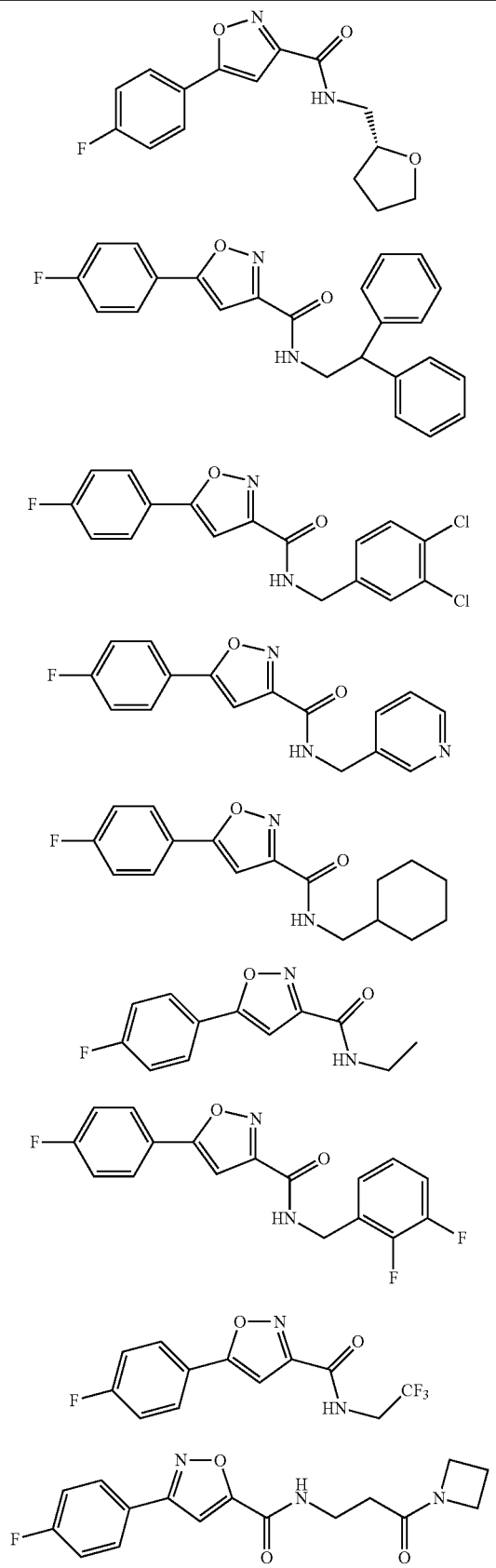

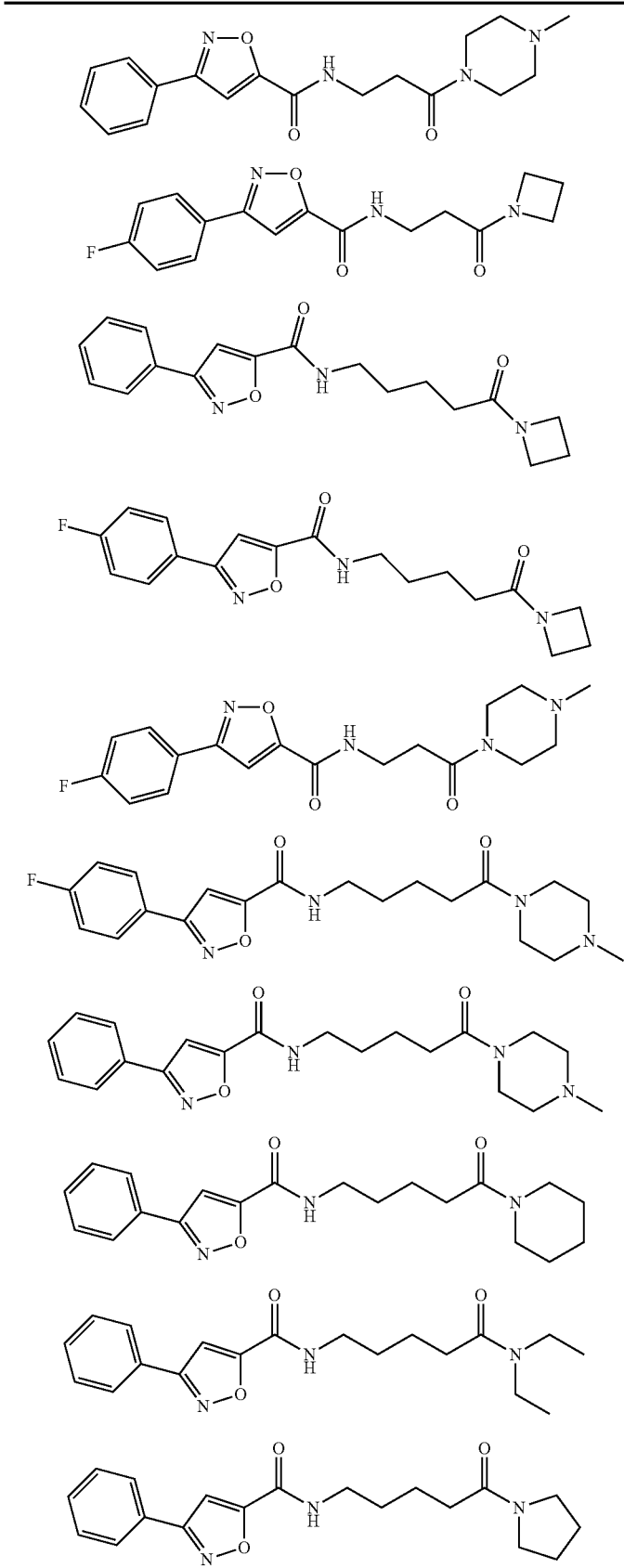

-continued

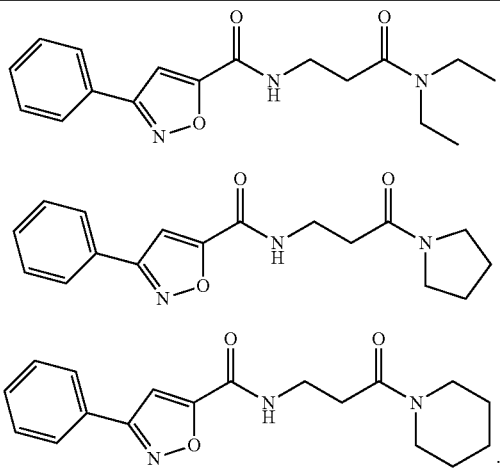

13. The method of claim 1, wherein the disease or disorder is cystic fibrosis.

14. The method of claim 13, further comprising administering to the subject a compound selected from Gentamicin, Genestein, Ataluren, Ivacaftor (Kalydeco), VX-661 and VX-809.

15. The method of claim 10, wherein the disease or disorder is cystic fibrosis.

16. The method of claim 12, wherein the disease or disorder is cystic fibrosis.

* * * * *

UNITED STATES PATENT AND TRADEMARK OFFICE
CERTIFICATE OF CORRECTION

PATENT NO. : 9,855,249 B2  
APPLICATION NO. : 14/873933  
DATED : January 2, 2018  
INVENTOR(S) : Bridget M. Cole and Andrew Kolodziej Page 1 of 2

It is certified that error appears in the above-identified patent and that said Letters Patent is hereby corrected as shown below:

In the Claims

At Column 74, Claim 8, Line 30:

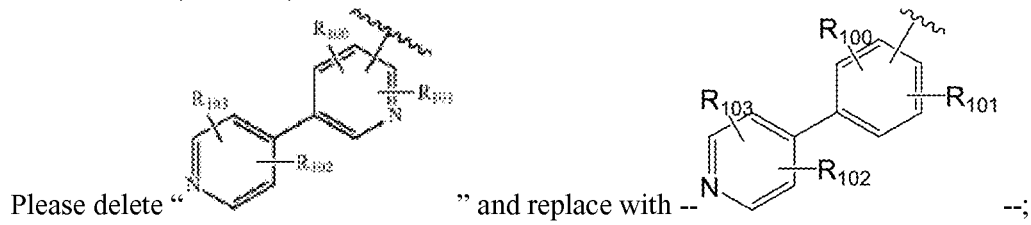

At Column 75, Claim 8, Line 25:

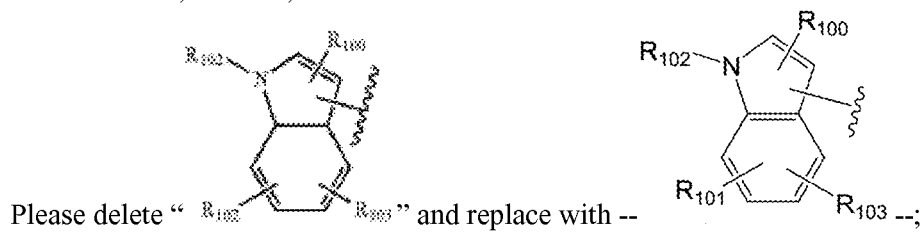

At Column 75, Claim 8, Line 30:

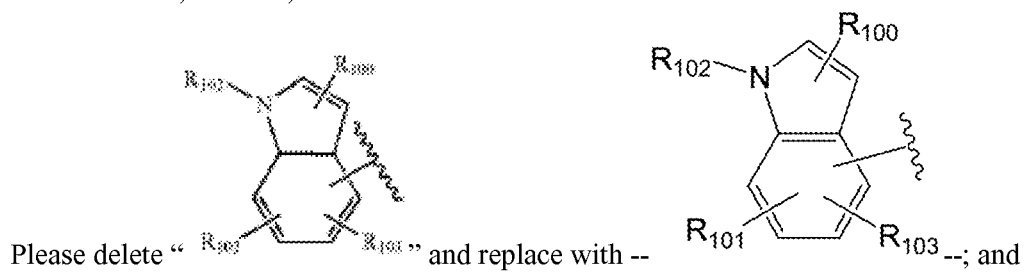

Signed and Sealed this  
Twenty-sixth Day of June, 2018

Andrei Iancu  
*Director of the United States Patent and Trademark Office*

CERTIFICATE OF CORRECTION (continued)
U.S. Pat. No. 9,855,249 B2

At Column 89, Claim 12:

Please delete the second structure " 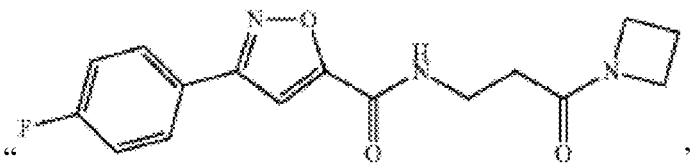 " and replace with -- 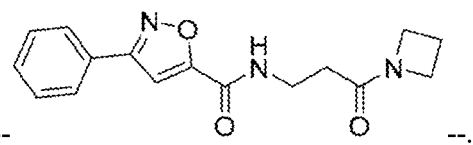 --.